US008404684B2

(12) United States Patent
Bruce et al.

(10) Patent No.: US 8,404,684 B2
(45) Date of Patent: Mar. 26, 2013

(54) INHIBITORS OF PHOSPHATIDYLINOSITOL 3-KINASE

(75) Inventors: Ian Bruce, Horsham (GB); Bernard Cuenoud, Lausanne (CH); Thomas Hugo Keller, Singapore (SG); Gaynor Elizabeth Pilgrim, Newark (GB); Nicola Press, Horsham (GB); Darren Mark Le Grand, Horsham (GB); Cathy Ritchie, Horsham (GB); Barbara Valade, Horsham (GB); Judy Hayler, Horsham (GB); Emma Budd, Horsham (GB)

(73) Assignee: Novartis AG, Basel (CH)

( * ) Notice: Subject to any disclaimer, the term of this patent is extended or adjusted under 35 U.S.C. 154(b) by 23 days.

(21) Appl. No.: 13/005,132

(22) Filed: Jan. 12, 2011

(65) Prior Publication Data

US 2011/0105535 A1    May 5, 2011

Related U.S. Application Data

(62) Division of application No. 10/554,559, filed as application No. PCT/EP2004/004603 on Apr. 30, 2004, now abandoned.

(30) Foreign Application Priority Data

May 2, 2003 (GB) .................................. 0310234.0

(51) Int. Cl.
C07D 417/04 (2006.01)
A61K 31/506 (2006.01)

(52) U.S. Cl. ..................... 514/235.8; 514/256; 544/122; 544/333

(58) Field of Classification Search .................. 544/122, 544/333; 514/235.8, 256
See application file for complete search history.

(56) References Cited

U.S. PATENT DOCUMENTS

| | | | |
|---|---|---|---|
| 4,649,146 A | 3/1987 | Takaya et al. | |
| 4,735,957 A | 4/1988 | Takaya et al. | |
| 6,187,797 B1 | 2/2001 | Pruitt et al. | |
| 2007/0032487 A1 | 2/2007 | Bruce et al. | |
| 2009/0030024 A1 | 1/2009 | Greul et al. | |
| 2009/0036654 A1 | 2/2009 | Jacobs et al. | |
| 2009/0163469 A1 | 6/2009 | Caravatti et al. | |
| 2010/0105711 A1 | 4/2010 | Fairhurst et al. | |
| 2010/0298286 A1 | 11/2010 | Fairhurst et al. | |
| 2011/0003818 A1 | 1/2011 | Fairhurst et al. | |

FOREIGN PATENT DOCUMENTS

| | | |
|---|---|---|
| EP | 0 117 082 A2 | 8/1984 |
| EP | 0 280 873 A1 | 9/1988 |
| EP | 0 373 226 B1 | 6/1994 |
| EP | 1 256 578 A1 | 11/2002 |
| EP | 1 256 578 B1 | 1/2006 |
| GB | 2 361 236 A | 10/2001 |
| WO | WO 89/09767 A1 | 10/1989 |
| WO | WO 98/27108 A2 | 6/1998 |
| WO | WO 99/21555 A2 | 5/1999 |
| WO | WO 99/65884 A1 | 12/1999 |
| WO | WO 01/17995 A1 | 3/2001 |
| WO | WO 01/72745 A1 | 10/2001 |
| WO | WO 02/32872 A1 | 4/2002 |
| WO | WO 03/015773 A2 | 2/2003 |
| WO | WO 03/015778 A1 | 2/2003 |
| WO | WO 03/029248 A1 | 4/2003 |
| WO | WO 03/072557 A1 | 9/2003 |
| WO | WO 2004/041813 A1 | 5/2004 |
| WO | WO 2004/045518 A2 | 6/2004 |
| WO | WO 2004/078754 A1 | 9/2004 |
| WO | WO 2004/096797 A1 | 11/2004 |
| WO | WO 2005/021519 A2 | 3/2005 |
| WO | WO 2005/026137 A2 | 3/2005 |
| WO | WO 2005/068444 A2 | 7/2005 |
| WO | WO 2006/051270 A1 | 5/2006 |
| WO | WO 2006/125805 A1 | 11/2006 |
| WO | WO 2006/125807 A1 | 11/2006 |
| WO | WO 2007/033780 A2 | 3/2007 |
| WO | WO 2007/068473 A2 | 6/2007 |
| WO | WO 2007/070600 A2 | 6/2007 |
| WO | WO 2007/082956 A1 | 7/2007 |
| WO | WO 2007/134827 A1 | 11/2007 |
| WO | WO 2008/064218 A2 | 5/2008 |
| WO | WO 2008/124000 A2 | 10/2008 |
| WO | WO 2008/145616 A1 | 12/2008 |
| WO | WO 2009/003009 A1 | 12/2008 |
| WO | WO 2009/012482 A2 | 1/2009 |
| WO | WO 2009/080694 A2 | 7/2009 |

(Continued)

OTHER PUBLICATIONS

Gura, Systems for identifying New Drugs are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*

(Continued)

Primary Examiner — Deepak Rao
(74) Attorney, Agent, or Firm — Scott W Reid

(57) ABSTRACT

Compounds of formula I

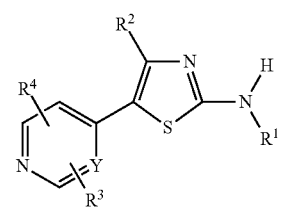

in free or salt form, wherein $R^1$, $R^2$, $R^3$ and $R^4$ have the meanings as indicated in the specification, are useful for treating conditions that are mediated by phosphatidylinositol 3-kinase.
Pharmaceutical compositions that contain the compounds and a process for preparing the compounds are also described.

10 Claims, No Drawings

FOREIGN PATENT DOCUMENTS

WO     WO 2009/080705 A2     7/2009

OTHER PUBLICATIONS

Kulkarni et al., CAPLUS Abstract 106:67261 (1987), 2 pgs.

Kulkarni et al., Chemical Abstracts 106:67261 (1986), see cpds. with Registry Nos. 106535-02-8 and 106534-99-0, 2 pgs.

Kulkarni et al., "Reactions of O-Amiothiophenol, Guanidine, Thiourea, Hydrazine Hydrate & Hydroxylamine with Acryloylthiazoles & Microbial Activities of the Reaction Products", Indian J. of Chem., Section B: Organic, Incl. Medicinal, Pub. & Info. Directorate, vol. 25B (1986), pp. 452-455.

Reddy et al., CAPLUS Abstract 105:39172 (1986), 3 pgs.

Simone, "Oncology: Introduction", Cecil Textbook of Medicine, 20$^{th}$ Edition, vol. 1 (1996), pp. 1004-1010.

Fry et al., "Phosphoinositide 3-kinase signaling in breast cancer: how big a role might it play?", Breast Cancer Research, vol. 3, No. 5 (2001), pp. 304-312.

Bruce, U.S. PTO Notice of Allowance, U.S. Appl. No. 10/554,559, Oct. 14, 2010, 6 pgs.

Bruce, U.S. PTO Office Action, U.S. Appl. No. 10/554,559, Jul. 8, 2010, 6 pgs.

Bruce, U.S. PTO Office Action, U.S. Appl. No. 10/554,559, Jan. 20, 2010, 10 pgs.

Bruce, U.S. PTO Office Action, U.S. Appl. No. 10/554,559, Aug. 24, 2009, 15 pgs.

Bruce, U.S. PTO Office Action, U.S. Appl. No. 10/554,559, Feb. 25, 2009, 6 pgs.

Berge et al., "Pharmaceutical Salts", Journal of Pharmaceutical Sciences, vol. 66, No. 1 (1977), pp. 1-19.

Luo et al., "Principles of Cancer Therapy: Oncogene and Non-oncogene Addiction", Cell vol. 136 (2009), pp. 823-837.

\* cited by examiner

INHIBITORS OF PHOSPHATIDYLINOSITOL 3-KINASE

CROSS-REFERENCE TO RELATED PATENT APPLICATIONS

This application is a Divisional of U.S. application Ser. No. 10/554,559, filed Jul. 17, 2006, which is the National Stage of International Application No. PCT/EP04/04603, filed Apr. 30, 2004, which is based upon and claims the benefit of priority from prior United Kingdom Patent Application No. 0310234.0, filed May 2, 2003, the entire contents of all of which are incorporated herein by reference in their entirety.

BACKGROUND OF THE INVENTION

The present invention relates to organic compounds, their preparation and their use as pharmaceuticals.

DESCRIPTION OF THE INVENTION

In a first aspect, the present invention provides compounds of formula I

I in free or salt form, wherein $R^1$ is $C_1$-$C_8$-alkylcarbonyl optionally substituted by halo, hydroxy, cyano, amino, carboxy, $C_1$-$C_8$-alkyl, $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)aminocarbonyl, $C_1$-$C_8$-alkylcarbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur, or $R^1$ is a 5- or 6-membered heterocyclic ring having one or more ring hetero atoms selected from the group consisting of oxygen, nitrogen and sulphur, or $R^1$ is aminocarbonyl optionally substituted by a $C_3$-$C_{15}$-carbocycle or by a 5- or 6-membered heterocyclic ring having one or more ring hetero atoms selected from the group consisting of oxygen, nitrogen and sulphur, or $R^1$ is —CO—$NR^xR^y$, where $R^x$ and $R^y$ together with the nitrogen to which they are attached form a 5- to 12-membered N-heterocyclic ring optionally including one or more ring hetero atoms selected from the group consisting of oxygen, nitrogen and sulphur, or $R^1$ is $C_1$-$C_8$-alkylaminocarbonyl or $C_3$-$C_8$-cycloalkylaminocarbonyl in either case optionally substituted in the alkyl group by halo, hydroxy, cyano, amino, carboxy, $C_1$-$C_8$-alkyl, $C_1$-$C_8$-alkoxy, hydroxy-substituted $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)amino-carbonyl, $C_1$-$C_8$-alkoxycarbonyl, a $C_3$-$C_{15}$-carbocycle, a 5- or 6-membered heterocyclic ring having one or more ring hetero atoms selected from the group consisting of oxygen, nitrogen and sulphur, or $C_1$-$C_8$-alkylaminocarbonyl optionally substituted by hydroxy, or $R^1$ is $C_1$-$C_8$-alkylaminocarbonyl or $C_3$-$C_8$-cycloalkylaminocarbonyl in either case optionally substituted by aminocarbonyl optionally substituted by a 5- or 6-membered heterocyclic ring having one or more ring hetero atoms selected from the group consisting of oxygen, nitrogen and sulphur, or $R^1$ is hydrogen;

$R^2$ is $C_1$-$C_3$-alkyl;

Y is carbon or nitrogen; and when $R^1$ is unsubstituted $C_1$-$C_8$-alkylcarbonyl and Y is carbon then $R^3$ is halo, hydroxy, cyano, amino, carboxy, —$SO_2NH_2$, $C_1$-$C_8$-alkyl, $C_1$-$C_8$-alkoxy, $C_1$-$C_8$-haloalkyl, amino-$C_1$-$C_8$-alkyl, amino-$C_1$-$C_8$-alkoxy, $C_1$-$C_8$-alkylaminocarbonyl, di($C_1$-$C_8$-alkyl)amino, di($C_1$-$C_8$-alkyl)aminocarbonyl, di($C_1$-$C_8$-alkyl)amino-$C_1$-$C_8$-alkyl, di($C_1$-$C_8$-alkyl)amino-$C_1$-$C_8$-alkoxy, aminocarbonyl, $C_1$-$C_8$-alkoxycarbonyl, carboxy-$C_1$-$C_8$-alkyl, carboxy-$C_1$-$C_8$-alkoxy, a $C_3$-$C_{15}$-carbocycle, a 5- or 6-membered heterocyclic ring having one or more ring hetero atoms selected from the group consisting of oxygen, nitrogen and sulphur, or $C_1$-$C_8$-alkylamino optionally substituted by hydroxy or di($C_1$-$C_8$-alkyl)amino, and $R^4$ is hydrogen, halo, hydroxy, cyano, amino, carboxy, —$SO_2NH_2$, $C_1$-$C_8$-alkyl, $C_1$-$C_8$-alkoxy, $C_1$-$C_8$-haloalkyl, amino-$C_1$-$C_8$-alkyl, amino-$C_1$-$C_8$-alkoxy, $C_1$-$C_8$-alkylaminocarbonyl, di($C_1$-$C_8$-alkyl)amino, di($C_1$-$C_8$-alkyl)aminocarbonyl, di($C_1$-$C_8$-alkyl)amino-$C_1$-$C_8$-alkyl, di($C_1$-$C_8$-alkyl)amino-$C_1$-$C_8$-alkoxy, aminocarbonyl, $C_1$-$C_8$-alkoxycarbonyl, carboxy-$C_1$-$C_8$-alkyl, carboxy-$C_1$-$C_8$-alkoxy, a $C_3$-$C_{15}$-carbocycle, a 5- or 6-membered heterocyclic ring having one or more ring hetero atoms selected from the group consisting of oxygen, nitrogen and sulphur, or $C_1$-$C_8$-alkylamino optionally substituted by hydroxy or di($C_1$-$C_8$-alkyl)amino, otherwise $R^3$ and $R^4$ are each independently hydrogen, halo, hydroxy, cyano, amino, carboxy, $C_1$-$C_8$-alkylsulfanyl, $C_1$-$C_8$-alkylsulfinyl, $C_1$-$C_8$-alkylsulfonyl, —$SO_2NH_2$, $C_1$-$C_8$-alkyl, $C_1$-$C_8$-haloalkyl, amino-$C_1$-$C_8$-alkyl, amino-$C_1$-$C_8$-alkoxy, $C_1$-$C_8$-alkylaminocarbonyl, di($C_1$-$C_8$-alkyl)aminocarbonyl, di($C_1$-$C_8$-alkyl)amino-$C_1$-$C_8$-alkyl, di($C_1$-$C_8$-alkyl)amino-$C_1$-$C_8$-alkoxy, $C_1$-$C_8$-acylamino, aminocarbonyl, $C_1$-$C_8$-alkoxycarbonyl, carboxy-$C_1$-$C_8$-alkyl, carboxy-$C_1$-$C_8$-alkoxy, a $C_3$-$C_{15}$-carbocycle, a 5- or 6-membered heterocyclic ring having one or more ring hetero atoms selected from the group consisting of oxygen, nitrogen and sulphur, $C_1$-$C_8$-alkylamino or di($C_1$-$C_8$-alkyl)amino each being optionally substituted by amino, hydroxy, di($C_1$-$C_8$-alkyl)amino or a 5- or 6-membered heterocyclic ring having one or more ring hetero atoms selected from the group consisting of oxygen, nitrogen and sulphur, or $C_1$-$C_8$-alkoxy optionally substituted by a 5- or 6-membered heterocyclic ring having one or more ring hetero atoms selected from the group consisting of oxygen, nitrogen and sulphur.

Terms used in the specification have the following meanings:

"Optionally substituted" as used herein means the group referred to can be substituted at one or more positions by any one or any combination of the radicals listed thereafter.

"Aminocarbonyl" as used herein denotes amino attached through the nitrogen atom to a carbonyl group.

"Halogen" or "halo" as used herein may be fluorine, chlorine, bromine or iodine; preferably it is fluorine or chlorine.

"$C_1$-$C_8$-alkyl" as used herein denotes straight chain or branched alkyl having 1 to 8 carbon atoms. Preferably, $C_1$-$C_8$-alkyl is $C_1$-$C_4$-alkyl.

"$C_3$-$C_{15}$-carbocyclic group" as used herein denotes a carbocyclic group having 3 to 15 ring carbon atoms, for example a monocyclic group, either cycloaliphatic, such as a $C_3$-$C_8$-cycloalkyl, for example cyclopentyl, cyclohexyl, cycloheptyl or cyclooctyl, or aromatic such as phenyl, or a bicyclic group such as bicyclooctyl, bicyclononyl including indanyl and indenyl, and bicyclodecyl including naphthyl. Preferably the $C_3$-$C_{15}$-carbocyclic group is a $C_3$-$C_{10}$-carbocyclic group, for example cyclopropyl, phenyl, or naphthyl. The $C_3$-$C_{15}$-carbocyclic group can be substituted or unsubstituted. Preferred substituents include halo, cyano, amino, nitro, carboxy, $C_1$-$C_8$-alkyl, halo-$C_1$-$C_8$-alkyl, $C_1$-$C_8$-alkoxy, $C_1$-$C_8$-alkylcarbonyl, $C_1$-$C_8$-alkylsulfonyl, —$SO_2NH_2$, a $C_3$-$C_{15}$-carbocyclic group and a 5- to 12-membered heterocyclic group having at least one ring heteroatom selected from nitrogen, oxygen and sulphur.

"$C_3$-$C_8$-cycloalkyl" as used herein denotes cycloalkyl having 3 to 8 ring carbon atoms, for example a monocyclic group such as a cyclopropyl, cyclobutyl, cyclopentyl, cyclohexyl, cycloheptyl or cyclooctyl, any of which can be substituted by one or more, usually one or two, $C_1$-$C_4$-alkyl groups, or a bicyclic group such as bicycloheptyl or bicyclooctyl. Preferably, "$C_3$-$C_8$-cycloalkyl" is $C_3$-$C_5$-cycloalkyl i.e. cyclopropyl, cyclobutyl or cyclopentyl.

"$C_1$-$C_8$-alkylsulfanyl" (or "$C_1$-$C_8$-alkylthio") as used herein denotes $C_1$-$C_8$-alkyl as hereinbefore defined linked to —S—. Preferably $C_1$-$C_8$-alkylsulfanyl is $C_1$-$C_4$-alkylsulfanyl, especially methylsulfanyl.

"$C_1$-$C_8$-alkylsulfinyl" as used herein denotes $C_1$-$C_8$-alkyl as hereinbefore defined linked to —S(=O)—. Preferably $C_1$-$C_8$-alkylsulfinyl is $C_1$-$C_4$-alkylsulfinyl, especially methylsulfinyl.

"$C_1$-$C_8$-alkylsulfonyl" as used herein denotes $C_1$-$C_8$-alkyl as hereinbefore defined linked to —$SO_2$—. Preferably $C_1$-$C_8$-alkylsulfonyl is $C_1$-$C_4$-alkylsulfonyl, especially methylsulfonyl".

"$C_1$-$C_8$-alkoxy" as used herein denotes straight chain or branched alkoxy having 1 to 8 carbon atoms. Preferably, $C_1$-$C_8$-alkoxy is $C_1$-$C_4$-alkoxy.

"$C_1$-$C_8$-haloalkyl" as used herein denotes $C_1$-$C_8$-alkyl as hereinbefore defined substituted by one or more halogen atoms, preferably one, two or three halogen atoms, preferably fluorine or chlorine atoms. Preferably, $C_1$-$C_8$-haloalkyl is $C_1$-$C_4$-alkyl substituted by one, two or three fluorine or chlorine atoms.

"Amino-$C_1$-$C_8$-alkyl" and "amino-$C_1$-$C_8$-alkoxy" as used herein denote amino attached by a nitrogen atom to $C_1$-$C_8$-alkyl or $C_1$-$C_8$-alkoxy respectively as hereinbefore defined.

Preferably, amino-$C_1$-$C_8$-alkyl and amino-$C_1$-$C_8$-alkoxy are respectively amino-$C_1$-$C_4$-alkyl and amino-$C_1$-$C_4$-alkoxy.

"Carboxy-$C_1$-$C_8$-alkyl" and "carboxy-$C_1$-$C_8$-alkoxy" as used herein denote carboxy attached by a carbon atom to $C_1$-$C_8$-alkyl or $C_1$-$C_8$-alkoxy respectively as hereinbefore defined. Preferably, carboxy-$C_1$-$C_8$-alkyl and carboxy-$C_1$-$C_8$-alkoxy are respectively carboxy-$C_1$-$C_4$-alkyl and carboxy-$C_1$-$C_4$-alkoxy.

"$C_1$-$C_8$-alkylcarbonyl", "$C_1$-$C_8$-alkoxycarbonyl" and "$C_1$-$C_8$-haloalkylcarbonyl" as used herein denote $C_1$-$C_8$-alkyl, $C_1$-$C_8$-alkoxy or $C_1$-$C_8$-haloalkyl respectively as hereinbefore defined attached by a carbon atom to a carbonyl group. Preferably, $C_1$-$C_8$-alkylcarbonyl, $C_1$-$C_8$-alkoxycarbonyl and $C_1$-$C_8$-haloalkylcarbonyl are respectively $C_1$-$C_4$-alkylcarbonyl, $C_1$-$C_4$-alkoxycarbonyl and $C_1$-$C_4$-haloalkyl-carbonyl.

"$C_1$-$C_8$-alkylamino", "di($C_1$-$C_8$-alkyl)amino" and "$C_3$-$C_8$-cycloalkylamino" as used herein denote $C_1$-$C_8$-alkyl, $C_1$-$C_8$-alkoxy and $C_3$-$C_8$-cycloalkyl respectively as hereinbefore defined attached by a carbon atom to an amino group. The $C_1$-$C_8$-alkyl groups in di($C_1$-$C_8$-alkyl)-amino may be the same or different. Preferably, $C_1$-$C_8$-alkylamino, di($C_1$-$C_8$-alkyl)amino and $C_3$-$C_8$-cycloalkylamino are respectively $C_1$-$C_4$-alkylamino, di($C_1$-$C_4$-alkyl)amino and $C_3$-$C_5$-cycloalkylamino.

"$C_1$-$C_8$-alkylaminocarbonyl", "di($C_1$-$C_8$-alkyl)aminocarbonyl" and "$C_3$-$C_8$-cycloalkylamino-carbonyl" as used herein denote $C_1$-$C_8$-alkylamino, di($C_1$-$C_8$-alkyl)amino and $C_3$-$C_8$ cycloalkylamino respectively as hereinbefore defined attached by a nitrogen atom to the carbon atom of a carbonyl group. Preferably, $C_1$-$C_8$-alkylaminocarbonyl, di($C_1$-$C_8$-alkyl)-aminocarbonyl and $C_3$-$C_8$-cycloalkylaminocarbonyl are respectively $C_1$-$C_4$-alkylaminocarbonyl, di($C_1$-$C_4$-alkyl)-aminocarbonyl and $C_3$-$C_5$-cycloalkylaminocarbonyl.

"di($C_1$-$C_8$-alkyl)amino-$C_1$-$C_8$-alkyl" and "di($C_1$-$C_8$-alkyl)amino-$C_1$-$C_8$-alkoxy" as used herein denote di($C_1$-$C_8$-alkyl)amino as hereinbefore defined attached by a nitrogen atom to the carbon atom of a $C_1$-$C_8$-alkyl or a $C_1$-$C_8$-alkoxy group respectively. Preferably, di($C_1$-$C_8$-alkyl)amino-$C_1$-$C_8$-alkyl and di($C_1$-$C_8$-alkyl)amino-$C_1$-$C_8$-alkoxy are respectively di($C_1$-$C_4$-alkyl)amino-$C_1$-$C_4$-alkyl and di($C_1$-$C_4$-alkyl)amino-$C_1$-$C_4$-alkoxy.

"$C_1$-$C_8$-acylamino" as used herein denotes amino substituted by $C_1$-$C_8$-alkylcarbonyl as hereinbefore defined. Preferably $C_1$-$C_8$-acylamino is $C_1$-$C_4$-acylamino, especially acetylamino.

"5- or 6-membered heterocyclic ring containing at least one ring heteroatom selected from the group consisting of nitrogen, oxygen and sulphur" as used herein may be, for example, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, morpholino, triazine, oxazine or thiazole. Preferred heterocyclic rings include piperazine, pyrrolidine, morpholino, imidazole, isotriazole, pyrazole, tetrazole, thiazole, thiadiazole, pyridine, piperidine, pyrazine, furan, oxazole, isoxazole, oxadiazole and azetidine. The 5- or 6-membered heterocyclic ring can be unsubstituted or substituted. Preferred substituents include halo, cyano, oxo, hydroxy, carboxy, nitro, $C_1$-$C_8$-alkyl, $C_1$-$C_8$-alkylsulfonyl, aminocarbonyl, $C_1$-$C_8$-alkylcarbonyl and $C_1$-$C_8$-alkoxy optionally substituted by aminocarbonyl. Especially preferred substituents include halo, oxo, hydroxy, $C_1$-$C_4$-alkyl, $C_1$-$C_4$-alkylsulfonyl, $C_1$-$C_4$-alkylcarbonyl and aminocarbonyl.

"5- to 12-membered N-heterocyclic ring optionally including one or more ring hetero atoms selected from the group consisting of oxygen, nitrogen and sulphur" as used herein may be, for example, azetidine, pyrrolidine, imidazolidine, piperidine, piperazine, morpholino or tetrahydro-imidazopyridine. The 5- to 12-membered N-heterocyclic ring is preferably a 5- to 9-membered N-heterocyclic ring. Preferred 5- to 12-membered N-heterocyclic rings include pyrrolidine, morpholino and tetrahydro-imidazo-pyridine. The 5- to 12-membered N-heterocyclic ring can be unsubstituted or substituted. Preferred substituents include halo, cyano, oxo, hydroxy, carboxy, nitro, $C_1$-$C_8$-alkylcarbonyl, —$SO_2$—$CH_3$, and $C_1$-$C_8$-alkyl or $C_1$-$C_8$-alkoxy in each case optionally substituted by carboxy, aminocarbonyl, $C_1$-$C_8$-alkoxy-carbonyl, or $C_1$-$C_5$-alkylaminocarbonyl or di($C_1$-$C_4$-alkyl)aminocarbonyl in each case being optionally substituted by hydroxy. Especially preferred substituents include hydroxy, —$SO_2$—$CH_3$ and aminocarbonyl.

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

In a second aspect, the present invention provides compounds of formula I

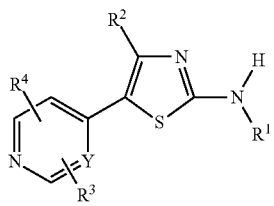

in free or salt form, wherein $R^1$ is $C_1$-$C_8$-alkylcarbonyl optionally substituted by halo, hydroxy, cyano, amino, carboxy, $C_1$-$C_8$-alkyl, $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)aminocarbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur, or $R^1$ is a 5- or 6-membered heterocyclic ring having one or more ring hetero atoms selected from the group consisting of oxygen, nitrogen and sulphur, or $R^1$ is aminocarbonyl optionally substituted by a $C_3$-$C_{15}$-carbocycle or by a 5- or 6-membered heterocyclic ring having one or more ring hetero atoms selected from the group consisting of oxygen, nitrogen and sulphur, or $R^1$ is $C_1$-$C_8$-alkylaminocarbonyl or $C_3$-$C_8$-cycloalkylaminocarbonyl in either case optionally substituted in the alkyl group by halo, hydroxy, cyano, amino, carboxy, $C_1$-$C_8$-alkyl, $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)amino-carbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur;

$R^2$ is $C_1$-$C_3$-alkyl;

Y is carbon or nitrogen; and when $R^1$ is unsubstituted $C_1$-$C_8$-alkylcarbonyl and Y is carbon then $R^3$ is [not hydrogen] halo, hydroxy, cyano, amino, carboxy, —$SO_2NH_2$, $C_1$-$C_8$-alkyl, $C_1$-$C_8$-alkoxy, $C_1$-$C_8$-haloalkyl, amino-$C_1$-$C_8$-alkyl, amino-$C_1$-$C_8$-alkoxy, $C_1$-$C_8$-alkylaminocarbonyl, di($C_1$-$C_8$-alkyl)amino, di($C_1$-$C_8$-alkyl)aminocarbonyl, di($C_1$-$C_8$-alkyl)amino-$C_1$-$C_8$-alkyl, di($C_1$-$C_8$-alkyl)amino-$C_1$-$C_8$-alkoxy, aminocarbonyl, $C_1$-$C_8$-alkoxycarbonyl, carboxy-$C_1$-$C_8$-alkyl, carboxy-$C_1$-$C_8$-alkoxy, a $C_3$-$C_{15}$-carbocycle, a 5- or 6-membered heterocyclic ring having one or more ring hetero atoms selected from the group consisting of oxygen, nitrogen and sulphur, or $C_1$-$C_8$-alkylamino optionally substituted by hydroxy or di($C_1$-$C_8$-alkyl)amino, and $R^4$ is hydrogen, halo, hydroxy, cyano, amino, carboxy, —$SO_2NH_2$, $C_1$-$C_8$-alkyl, $C_1$-$C_8$-alkoxy, $C_1$-$C_8$-haloalkyl, amino-$C_1$-$C_8$-alkyl, amino-$C_1$-$C_8$-alkoxy, $C_1$-$C_8$-alkylaminocarbonyl, di($C_1$-$C_8$-alkyl)amino, di($C_1$-$C_8$-alkyl)aminocarbonyl, di($C_1$-$C_8$-alkyl)amino-$C_1$-$C_8$-alkyl, di($C_1$-$C_8$-alkyl)amino-$C_1$-$C_8$-alkoxy, aminocarbonyl, $C_1$-$C_8$-alkoxycarbonyl, carboxy-$C_1$-$C_8$-alkyl, carboxy-$C_1$-$C_8$-alkoxy, a $C_3$-$C_{15}$-carbocycle, a 5- or 6-membered heterocyclic ring having one or more ring hetero atoms selected from the group consisting of oxygen, nitrogen and sulphur, or $C_1$-$C_8$-alkylamino optionally substituted by hydroxy or di($C_1$-$C_8$-alkyl)amino, otherwise $R^3$ and $R^4$ are each independently hydrogen, halo, hydroxy, cyano, amino, carboxy, —$SO_2NH_2$, $C_1$-$C_8$-alkyl, $C_1$-$C_8$-alkoxy, $C_1$-$C_8$-haloalkyl, amino-$C_1$-$C_8$-alkyl, amino-$C_1$-$C_8$-alkoxy, $C_1$-$C_8$-alkylaminocarbonyl, di($C_1$-$C_8$-alkyl)amino, di($C_1$-$C_8$-alkyl)aminocarbonyl, di($C_1$-$C_8$-alkyl)amino-$C_1$-$C_8$-alkyl, di($C_1$-$C_8$-alkyl)amino-$C_1$-$C_8$-alkoxy, aminocarbonyl, $C_1$-$C_8$-alkoxycarbonyl, carboxy-$C_1$-$C_8$-alkyl, carboxy-$C_1$-$C_8$-alkoxy, a $C_3$-$C_{15}$-carbocycle, a 5- or 6-membered heterocyclic ring having one or more ring hetero atoms selected from the group consisting of oxygen, nitrogen and sulphur, or $C_1$-$C_8$-alkylamino optionally substituted by hydroxy or di($C_1$-$C_8$-alkyl)amino Preferred compounds of the present invention include compounds of formula I in free or salt form, wherein $R^1$ is $C_1$-$C_8$-alkylcarbonyl optionally substituted by di($C_1$-$C_8$-alkyl)amino, $C_1$-$C_8$-alkylcarbonyl or $C_1$-$C_8$-alkoxycarbonyl, or $R^1$ is a 5- or 6-membered heterocyclic ring having one or more ring hetero atoms selected from the group consisting of oxygen, nitrogen and sulphur, or $R^1$ is —CO—$NR^xR^y$, where $R^x$ and $R^y$ together with the nitrogen to which they are attached form a 5- to 12-membered N-heterocyclic ring optionally including one or more ring hetero atoms selected from the group consisting of oxygen, nitrogen and sulphur, or $R^1$ is $C_1$-$C_8$-alkylaminocarbonyl optionally substituted in the alkyl group by hydroxy, $C_1$-$C_8$-alkoxy, hydroxy-substituted $C_1$-$C_8$-alkoxy, di($C_1$-$C_8$-alkyl)amino, di($C_1$-$C_8$-alkyl)amino-carbonyl, $C_1$-$C_8$-alkoxycarbonyl, a 5- or 6-membered heterocyclic ring having one or more ring hetero atoms selected from the group consisting of oxygen, nitrogen and sulphur, or $C_1$-$C_8$-alkylaminocarbonyl optionally substituted by hydroxy, or $R^1$ is $C_1$-$C_8$-alkylaminocarbonyl optionally substituted by aminocarbonyl optionally substituted by a 5- or 6-membered heterocyclic ring having one or more ring hetero atoms selected from the group consisting of oxygen, nitrogen and sulphur, or $R^1$ is hydrogen;

$R^2$ is $C_1$-$C_3$-alkyl;

Y is carbon or nitrogen; and when $R^1$ is unsubstituted $C_1$-$C_8$-alkylcarbonyl and Y is carbon then $R^3$ is halo, $C_1$-$C_8$-alkyl or a 5- or 6-membered heterocyclic ring having one or more ring hetero atoms selected from the group consisting of oxygen, nitrogen and sulphur, and $R^4$ is hydrogen or $C_1$-$C_8$-alkyl, otherwise $R^3$ and $R^4$ are each independently hydrogen, halo, cyano, $C_1$-$C_8$-alkylsulfanyl, $C_1$-$C_8$-alkylsulfinyl, $C_1$-$C_8$-alkylsulfonyl, $C_1$-$C_8$-alkyl, $C_1$-$C_8$-acylamino, a $C_3$-$C_{15}$-carbocycle, a 5- or 6-membered heterocyclic ring having one or more ring hetero atoms selected from the group consisting of oxygen, nitrogen and sulphur, $C_1$-$C_8$-alkylamino or di($C_1$-$C_8$-alkyl)amino each being optionally substituted by amino, hydroxy, di($C_1$-$C_8$-alkyl)amino or a 5- or 6-membered heterocyclic ring having one or more ring hetero atoms selected from the group consisting of oxygen, nitrogen and sulphur, or $C_1$-$C_8$-alkoxy optionally substituted by a 5- or 6-membered heterocyclic ring having one or more ring hetero atoms selected from the group consisting of oxygen, nitrogen and sulphur.

Preferred compounds of the present invention also include compounds of formula I in free or salt form, wherein $R^1$ is $C_1$-$C_8$-alkylcarbonyl or a 5- or 6-membered heterocyclic ring having one or more ring hetero atoms selected from the group consisting of oxygen, nitrogen and sulphur, or $R^1$ is $C_1$-$C_8$-alkylaminocarbonyl optionally substituted in the alkyl group by $C_1$-$C_8$-alkoxycarbonyl, di($C_1$-$C_8$-alkyl) aminocarbonyl or by a 5- or 6-membered heterocyclic ring having one or more ring hetero atoms selected from the group consisting of oxygen, nitrogen and sulphur;

$R^2$ is $C_1$-$C_3$-alkyl;

Y is carbon or nitrogen; and when $R^1$ is unsubstituted $C_1$-$C_8$-alkylcarbonyl and Y is carbon then $R^3$ is halo, $C_1$-$C_8$-alkyl or a 5- or 6-membered heterocyclic ring having one or more ring hetero atoms selected from the group consisting of oxygen, nitrogen and sulphur, and $R^4$ is hydrogen or $C_1$-$C_8$-alkyl, otherwise $R^3$ and $R^4$ are each independently hydrogen, halo, $C_1$-$C_8$-alkyl, $C_3$-$C_8$-cycloalkyl, a 5- or 6-membered heterocyclic ring having one or more ring hetero atoms selected from the group consisting of oxygen, nitrogen and sulphur, or $C_1$-$C_8$-alkylamino optionally substituted by hydroxy or di($C_1$-$C_8$-alkyl)amino Especially preferred compounds of the present invention include compounds of formula I in free or salt form, wherein $R^1$ is $C_1$-$C_4$-alkylcarbonyl optionally substituted by di($C_1$-$C_4$-alkyl)amino, $C_1$-$C_4$-alkylcarbonyl or $C_1$-$C_4$-alkoxycarbonyl, or $R^1$ is a 5- or 6-membered heterocyclic ring having one or more ring hetero atoms selected from the group consisting of oxygen, nitrogen and sulphur, or $R^1$ is —CO—$NR^xR^y$, where $R^x$ and $R^y$ together with the nitrogen to which they are attached form a 5- to 9-membered N-heterocyclic ring optionally including one or more ring hetero atoms selected from the group consisting of oxygen, nitrogen and sulphur, or $R^1$ is $C_1$-$C_4$-alkylaminocarbonyl optionally substituted in the alkyl group by hydroxy, $C_1$-$C_4$-alkoxy, hydroxy-substituted $C_1$-$C_4$-alkoxy, di($C_1$-$C_4$-alkyl)amino, di($C_1$-$C_4$-alkyl)amino-carbonyl, $C_1$-$C_4$-alkoxycarbonyl, a 5- or 6-membered heterocyclic ring having one or more ring hetero atoms selected from the group consisting of oxygen, nitrogen and sulphur, $C_1$-$C_4$-alkylaminocarbonyl optionally substituted by hydroxy, or by $C_1$-$C_4$-alkoxy, or $R^1$ is $C_1$-$C_4$-alkylaminocarbonyl optionally substituted by aminocarbonyl optionally substituted by a 5- or 6-membered heterocyclic ring having one or more ring hetero atoms selected from the group consisting of oxygen, nitrogen and sulphur, or $R^1$ is hydrogen;

$R^2$ is $C_1$-$C_3$-alkyl;

Y is carbon or nitrogen; and when $R^1$ is unsubstituted $C_1$-$C_4$-alkylcarbonyl and Y is carbon then $R^3$ is halo, $C_1$-$C_4$-alkyl or a 5- or 6-membered heterocyclic ring having one or more ring hetero atoms selected from the group consisting of oxygen, nitrogen and sulphur, and $R^4$ is hydrogen or $C_1$-$C_4$-alkyl, otherwise $R^3$ and $R^4$ are each independently hydrogen, halo, cyano, $C_1$-$C_4$-alkylsulfanyl, $C_1$-$C_4$-alkylsulfinyl, $C_1$-$C_4$-alkylsulfonyl, $C_1$-$C_4$-alkyl, $C_1$-$C_4$-acylamino, a $C_3$-$C_{10}$-carbocycle, a 5- or 6-membered heterocyclic ring having one or more ring hetero atoms selected from the group consisting of oxygen, nitrogen and sulphur, $C_1$-$C_4$-alkylamino or di($C_1$-$C_4$-alkyl)amino each being optionally substituted by amino, hydroxy, di($C_1$-$C_4$-alkyl)amino or a 5- or 6-membered heterocyclic ring having one or more ring hetero atoms selected from the group consisting of oxygen, nitrogen and sulphur, or $C_1$-$C_4$-alkoxy optionally substituted by a 5- or 6-membered heterocyclic ring having one or more ring hetero atoms selected from the group consisting of oxygen, nitrogen and sulphur.

Especially preferred compounds of the present invention also include compounds of formula I in free or salt form, wherein $R^1$ is $C_1$-$C_4$-alkylcarbonyl or a 5- or 6-membered N-heterocyclic ring having one or more ring hetero atoms selected from the group consisting of oxygen, nitrogen and sulphur, or $R^1$ is $C_1$-$C_4$-alkylaminocarbonyl optionally substituted in the alkyl group by $C_1$-$C_4$-alkoxycarbonyl, di($C_1$-$C_4$-alkyl) aminocarbonyl or by a 5- or 6-membered N-heterocyclic ring having one or more ring hetero atoms selected from the group consisting of oxygen, nitrogen and sulphur;

$R^2$ is $C_1$-$C_3$-alkyl;

Y is carbon or nitrogen; and when $R^1$ is unsubstituted $C_1$-$C_4$-alkylcarbonyl and Y is carbon then $R^3$ is halo, $C_1$-$C_4$-alkyl or a 5- or 6-membered N-heterocyclic ring having one or more ring hetero atoms selected from the group consisting of oxygen, nitrogen and sulphur, and $R^4$ is hydrogen or $C_1$-$C_4$-alkyl, otherwise $R^3$ and $R^4$ are each independently hydrogen, halo, $C_1$-$C_4$-alkyl, $C_3$-$C_5$-cycloalkyl, a 5- or 6-membered N-heterocyclic ring having one or more ring hetero atoms selected from the group consisting of oxygen, nitrogen and sulphur, or $C_1$-$C_4$-alkylamino optionally substituted by hydroxy or di($C_1$-$C_4$-alkyl)amino Many of the compounds represented by formula I are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids, for example aliphatic monocarboxylic acids such as formic acid, acetic acid, trifluoroacetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of formula I by known salt-forming procedures.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of formula I by known salt-forming procedures.

Specific preferred compounds of formula I are described hereinafter in the Examples.

The invention provides, in another aspect, a process for preparing a compound of formula I in free or salt form which comprises the steps of:
(i) (A) reacting a compound of formula II

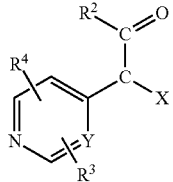

wherein $R^2$, $R^3$, $R^4$ and Y are as hereinbefore defined and X is halogen, with a compound of formula III

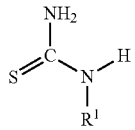

wherein $R^1$ is as hereinbefore defined;
(B) for the preparation of compounds of formula I where $R^3$ is a 5- or 6-membered N-heterocyclic ring having one or more ring hetero atoms selected from the group consisting of oxygen, nitrogen and sulphur, reacting a compound of formula I wherein $R^1$, $R^2$, $R^4$ and Y are as hereinbefore defined and $R^3$ is chloro or bromo, with a compound of formula IV

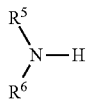

wherein $R^5$ and $R^6$ together form a 5- or 6-membered N-heterocyclic ring having one or more ring hetero atoms selected from the group consisting of oxygen, nitrogen and sulphur;
(C) for the preparation of compounds of formula I where $R^3$ is $C_1$-$C_8$-alkylamino optionally substituted by hydroxy or di($C_1$-$C_8$-alkyl)amino, reacting a compound of formula I wherein $R^1$, $R^2$, $R^4$ and Y are as hereinbefore defined and $R^3$ is chloro or bromo, with a compound of formula V

wherein $R^7$ is $C_1$-$C_8$-alkyl optionally substituted by hydroxy or di($C_1$-$C_8$-alkyl)amino;
(D) for the preparation of compounds of formula I where $R^1$ is $C_1$-$C_8$-alkylcarbonyl optionally substituted by halo, hydroxy, cyano, amino, carboxy, $C_1$-$C_8$-alkyl, $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)-aminocarbonyl, $C_1$-$C_8$-alkylcarbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur, reacting a compound of formula VI

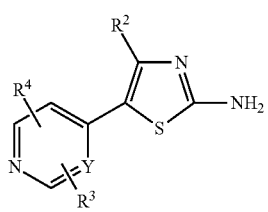

wherein $R^2$, $R^3$, $R^4$ and Y are as hereinbefore defined, with a compound of formula VII

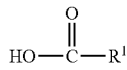

or an amide-forming derivative thereof such as an acid halide or anhydride wherein $R^1$ is $C_1$-$C_8$-alkylcarbonyl optionally substituted by halo, hydroxy, cyano, amino, carboxy, $C_1$-$C_8$-alkyl, $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)-aminocarbonyl, $C_1$-$C_8$-alkylcarbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur;
(E) for the preparation of compounds of formula I where $R^1$ is $C_1$-$C_8$-alkylamino-carbonyl optionally substituted by halo, hydroxy, cyano, amino, carboxy, $C_1$-$C_8$-alkyl, $C_1$-$C_8$-alkoxy, hydroxy-substituted $C_1$-$C_8$-alkoxy, $C_1$-$C_8$-haloalkyl, $C_1$-$C_8$-alkylamino, di($C_1$-$C_8$-alkyl) amino, di($C_1$-$C_8$-alkyl)aminocarbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur, or $C_1$-$C_8$-alkylaminocarbonyl optionally substituted by hydroxy, reacting a compound of formula VI wherein $R^2$, $R^3$, $R^4$ and Y are as hereinbefore defined, with a compound of formula VIII $$O=C=N-R^8 \qquad \text{VIII}$$

wherein $R^8$ is $C_1$-$C_8$-alkyl optionally substituted by halo, hydroxy, cyano, amino, carboxy, $C_1$-$C_8$-alkyl, $C_1$-$C_8$-alkoxy, hydroxy-substituted $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)aminocarbonyl, $C_1$-$C_8$-alkoxy-carbonyl, a $C_3$-$C_{15}$-carbocycle, a 5- or 6-membered heterocyclic ring having one or more ring hetero atoms selected from the group consisting of oxygen, nitrogen and sulphur, or $C_1$-$C_8$-alkylaminocarbonyl optionally substituted by hydroxy;
(F) for the preparation of compounds of formula I where $R^1$ is $C_1$-$C_8$-alkylamino-carbonyl optionally substituted by halo, hydroxy, cyano, amino, carboxy, $C_1$-$C_8$-alkyl, $C_1$-$C_8$-alkoxy, hydroxy-substituted $C_1$-$C_8$-alkoxy, $C_1$-$C_8$-haloalkyl, $C_1$-$C_8$-alkylamino, di($C_1$-$C_8$-alkyl) amino, di($C_1$-$C_8$-alkyl)aminocarbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur, or $C_1$-$C_8$-alkylaminocarbonyl optionally substituted by hydroxy, reacting a compound of formula IX

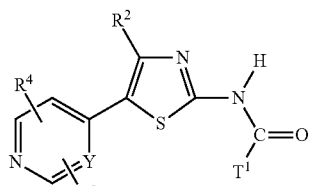

wherein $R^2$, $R^3$, $R^4$ and Y are as hereinbefore defined and $T^1$ is a 5- or 6-membered heterocyclic ring having one or more ring hetero atoms selected from the group consisting of oxygen, nitrogen and sulphur, with a compound of formula X $$R^9—NH_2 \quad\quad X$$

wherein $R^9$ is $C_1$-$C_8$-alkyl optionally substituted by halo, hydroxy, cyano, amino, carboxy, $C_1$-$C_8$-alkyl, $C_1$-$C_8$-alkoxy, hydroxy-substituted $C_1$-$C_8$-alkoxy, $C_1$-$C_8$-haloalkyl, $C_1$-$C_8$-alkylamino, di($C_1$-$C_8$-alkyl)amino, di($C_1$-$C_8$-alkyl)aminocarbonyl, $C_1$-$C_8$-alkoxycarbonyl, a $C_3$-$C_{15}$-carbocycle, or by a 5- or 6-membered heterocyclic ring having one or more ring hetero atoms selected from the group consisting of oxygen, nitrogen and sulphur, or $C_1$-$C_8$-alkylaminocarbonyl optionally substituted by hydroxy;

(G) for the preparation of compounds of formula I where $R^3$ is $C_1$-$C_8$-alkylsulfinyl or $C_1$-$C_8$-alkylsulfonyl, oxidising the corresponding $C_1$-$C_8$-alkylsulfanyl or $C_1$-$C_8$-alkylsulfinyl respectively;

(H) for the preparation of compounds of formula I where $R^3$ is di($C_1$-$C_8$-alkyl)amino optionally substituted by amino, hydroxy, di($C_1$-$C_8$-alkyl)amino or a 5- or 6-membered heterocyclic ring having one or more ring hetero atoms selected from the group consisting of oxygen, nitrogen and sulphur, reacting the corresponding compound where $R^3$ is $C_1$-$C_8$-alkylsulfinyl or $C_1$-$C_8$-alkylsulfonyl with a compound of formula Xa

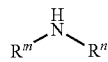
$$\quad\quad Xa$$

or a protected form thereof where $R^m$ and $R^n$ are independently $C_1$-$C_8$-alkyl optionally substituted by amino, hydroxy, di($C_1$-$C_8$-alkyl)amino or a 5- or 6-membered heterocyclic ring having one or more ring hetero atoms selected from the group consisting of oxygen, nitrogen and sulphur;

(I) for the preparation of compounds of formula I where $R^3$ is $C_1$-$C_8$-alkoxy, reacting the corresponding compound where $R^3$ is $C_1$-$C_8$-alkylsulfinyl with an alkali metal $C_1$-$C_8$-alkoxide;

(J) for the preparation of compounds of formula I where $R^3$ is $C_1$-$C_8$-alkoxy substituted by a 5- or 6-membered heterocyclic ring having one or more ring hetero atoms selected from the group consisting of oxygen, nitrogen and sulphur, reacting the corresponding compound where $R^3$ is $C_1$-$C_8$-alkylsulfinyl with a compound of formula Xb $$HO—V-T^2 \quad\quad Xb$$

where V is $C_1$-$C_8$-alkyl and $T^2$ is a 5- or 6-membered heterocyclic ring having one or more ring hetero atoms selected from the group consisting of oxygen, nitrogen and sulphur in the presence of a base; or (K) for the preparation of compounds of formula I where $R^3$ is cyano, reducing the corresponding compound where $R^3$ is $C_1$-$C_8$-alkylsulfonyl with an alkali metal cyanide; and (ii) removing any protecting groups and recovering the resultant compound of formula I in free or salt form.

Process variant (A) may be carried out using known procedures for preparing aminothiazoles, or analogously, e.g. as hereinafter described in the Examples. The halogen X is preferably bromine The reaction may be carried out in an organic solvent, e.g. an alcohol such as ethanol. The reaction temperature may be from room temperature to the reflux temperature of the solvent, but conveniently from about 50° C. to about 70° C.

Process variant (B) may be carried out using known procedures for reacting halides with nucleophilic N-heterocyclic rings, or analogously, e.g. as hereinafter described in the Examples. The reaction may be carried out in an organic solvent, e.g. dimethylsulphoxide (DMSO). The reaction temperature may be from room temperature to the reflux temperature of the solvent, but conveniently from about 80° C. to about 150° C. The temperature may be achieved by conventional heating or by microwave irradiation.

Process variant (C) may be carried out using known procedures for reacting heterocyclic halides with amines, or analogously, e.g. as hereinafter described in the Examples. The reaction may be carried out in an organic solvent, e.g. dimethylsulphoxide (DMSO). The reaction temperature may be from room temperature to the reflux temperature of the solvent, but conveniently from about 80° C. to about 150° C. The temperature may be achieved by conventional heating or by microwave irradiation.

Process variant (D) may be carried out using known procedures for reacting amines with carboxylic acids or an amide-forming derivative thereof such as an acid halide or anhydride, or analogously, e.g. as hereinafter described in the Examples. The reaction may be carried out in an organic solvent, for example dichloromethane (DCM). It is preferably carried out in the presence of a base, for example diisopropylethylamine (DIPEA). When the amine is reacted with a carboxylic acid it is preferred carried out in the presence of a peptide coupling agent, for example 1-hydroxybenzotriazole (HOBT). The reaction temperature may be from room temperature to the reflux temperature of the solvent, but conveniently from about 60° C. to about 80° C.

Process variant (E) may be carried out using known procedures for reacting amines with isocyanates, or analogously, e.g. as hereinafter described in the Examples. The reaction may be carried out in an organic solvent, e.g. DCM or dimethylformamide (DMF), preferably in the presence of a base, for example diisopropylethylamine (DIPEA). The reaction temperature may be from room temperature to the reflux temperature of the solvent, but conveniently from about 50° C. to about 70° C.

Process variant (F) may be carried out using known procedures for reacting carbonyl diheterocyclic intermediates (e.g. acylimidazolides when T is imidazole) with amines to form ureas, or analogously, e.g. as hereinafter described in the Examples. The reaction may be carried out in an organic solvent, e.g. dimethylformamide (DMF). The reaction temperature may be from about 10° C. to about 50° C., but conveniently room temperature.

Process variant (G) may be carried out using known procedures for oxidising sulfanyl groups to form sulfinyl groups or for oxidising sulfinyl groups to form sulfonyl groups or analogously e.g. as hereinafter described in the Examples. The oxidising agent used is preferably a perbenzoic acid, especially meta-chloroperoxybenzoic acid (m-CPBA). The reaction is conveniently carried out in an organic solvent such as dichloromethane (DCM). The reaction temperature may be e.g. from 0 to 30° C., preferably room temperature.

Process variant (H) may be carried out using known procedures for reacting sulfinyl groups or sulfonyl groups with secondary amines to form di(alkyl)amines or analogously e.g. as hereinafter described in the Examples. The reaction is conveniently carried out in an organic solvent such as DMF. The reaction temperature may be e.g. from 60 to 100° C., preferably from 70 to 90° C.

Process variant (I) may be carried out using known procedures for reacting alkylsulfinyl groups with alkali metal alkoxides to form alkoxy groups or analogously e.g. as hereinafter described in the Examples. The alkali metal alkoxide is preferably a sodium alkoxide. The reaction is conveniently carried out in an organic solvent such as methanol. The reaction temperature may be e.g. from 0 to 40° C., preferably room temperature.

Process variant (J) may be carried out using known procedures for reacting alkylsulfinyl groups with substituted primary alcohols to form substituted alkoxy groups or analogously e.g. as hereinafter described in the Examples. The base is preferably a strong base such as sodium hydride. The reaction is conveniently carried out in an organic solvent such as DCM. The reaction temperature may be e.g. from 60 to 80° C., but preferably about 70° C.

Process variant (K) may be carried out using known procedures for reducing alkylsulfonyl groups to a cyano group or analogously e.g. as hereinafter described in the Examples. The alkali metal cyanide is preferably sodium cyanide. The reaction is conveniently carried out in an organic solvent such as dimethylsulphoxide (DMSO). The reaction temperature may be e.g. from 40 to 60° C., but preferably about 50° C.

The compounds of formula I in free or salt form can be recovered from reaction mixtures and purified in a conventional manner. Isomer mixtures can be separated into individual isomers, e.g. enantiomers, in a conventional manner, e.g. by fractional crystallisation.

Compounds of formula II may be prepared by reacting a compound of formula XI

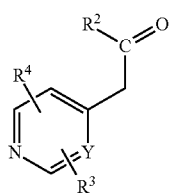

XI wherein $R^2$, $R^3$, $R^4$ and Y are as hereinbefore defined, with a halogenating agent, for example bromine, or analogously, for example as described in the Examples. The reaction may be carried out in an organic solvent, e.g. dioxane. The reaction temperature may be from about 0° C. to about 30° C., but conveniently about 10° C.

Compounds of formula III, IV and V are commercially available or may be prepared by known methods.

Compounds of formula VI where Y is carbon or nitrogen may be prepared by reacting a compound of formula II wherein $R^2$, $R^3$, $R^4$ and X are as hereinbefore defined and Y is carbon or nitrogen with thiourea, or analogously, for example as described in the Examples or as described in European patent specification EP 117082 A. The reaction may be carried out in an organic solvent, e.g. an alcohol such as ethanol. The reaction temperature may be from room temperature to the reflux temperature of the solvent, but conveniently from about 50° C. to about 70° C.

Compounds of formula VI where Y is nitrogen may be prepared by reacting a compound of formula XII

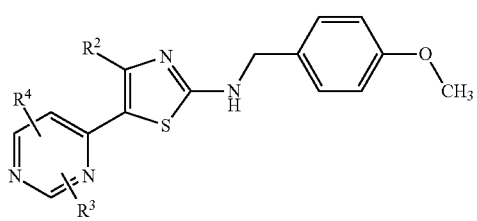

XII wherein $R^2$, $R^3$ and $R^4$ are as hereinbefore defined with an acid, for example trifluoroacetic acid, or analogously, for example as described in the Examples. The reaction may be carried out in a polar solvent, e.g. water. The reaction temperature may be from about 0 and 100° C., but preferably about 75° C.

Compounds of formula VII are commercially available or may be prepared by known methods.

Compounds of formula VIII are commercially available or may be prepared by known methods.

Compounds of formula IX may be prepared by reacting a compound of formula VI wherein $R^2$, $R^3$, $R^4$, and Y are as hereinbefore defined with a compound of formula XIII

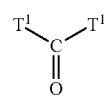

XIII wherein each $T^1$, which may be the same or different, is a 5- or 6-membered heterocyclic ring having one or more ring hetero atoms selected from the group consisting of oxygen, nitrogen and sulphur, or analogously, for example as described in the Examples. The compound of formula XIII is preferably carbonyl diimidazole (CDI). The reaction may be carried out in an organic solvent, e.g. dichloromethane (DCM). The reaction temperature may be from 20° C. to about 60° C., but conveniently about 40° C.

Compounds of formula X, Xa or Xb are commercially available or may be prepared by known methods.

Compounds of formula XI are commercially available or may be prepared by reacting a compound of formula XIV

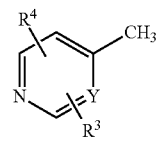

XIV wherein $R^3$, $R^4$ and Y are as hereinbefore defined with a base, such as butyllithium (n-BuLi) or lithium diisopropyl amide (LDA), then adding of a compound of formula XV

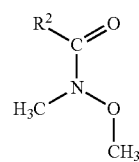

XV (a Weinreb amide) wherein $R^2$ is as hereinbefore using known procedures for reacting alkyl-substituted aromatic compounds with Weinreb amides, or analogously, for example as described in the Examples. The reaction may be carried out in an organic solvent, e.g. tetrahydrofuran (THF). The reaction temperature may be from −20° C. to about 10° C., but conveniently about 0° C.

Alternatively, compounds of formula XI wherein $R^3$, $R^4$ and Y are as hereinbefore defined and $R^2$ is methyl may be prepared by reacting a compound of formula XIII wherein $R^3$, $R^4$ and Y are as hereinbefore defined with a base such as butyllithium (n-BuLi) or lithium diisopropyl amide (LDA), then adding ethyl acetate using known methods for reacting alkyl-substituted aromatic compounds with esters, or analogously, for example as described in the Examples. The reaction may be carried out in an organic solvent, e.g. tetrahydrofuran (THF). The reaction temperature may be from −10° C. to about 10° C., but conveniently about 0° C.

Compounds of formula XII may be prepared by reacting a compound of formula XVI

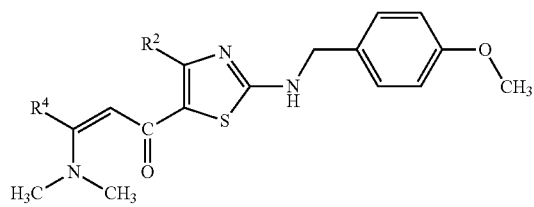

XVI wherein $R^2$ and $R^4$ are as hereinbefore defined, with a compound of formula XVII

XVII wherein $R^3$ is as hereinbefore defined using the procedure described in international patent specification WO 01/72745, or analogously, for example as described in the Examples.

Compounds of formula XIII, XIIV and XV are commercially available or may be prepared by known methods.

Compounds of formula XVI may be prepared by reacting a compound of formula XVIII

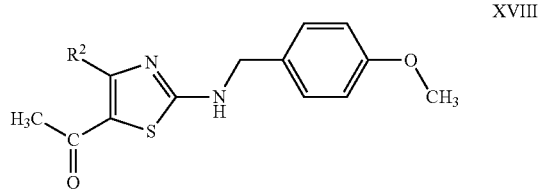

XVIII wherein $R^2$ is as hereinbefore defined, with a compound of formula XIX

XIX wherein $R^4$ is as hereinbefore defined using the procedure described in international patent specification WO 01/72745, or analogously, for example as described in the Examples.

Compounds of formula XVII are commercially available or may be prepared by known methods.

Compounds of formula XVIII may be prepared by reacting a compound of formula XX

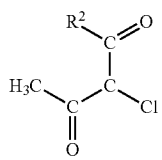

XX wherein $R^2$ is as hereinbefore defined with 2-thiourea or a protected form thereof (for example 1-(4-methoxybenzyl)-2-thiourea) in the presence of pyridine in methanol as described in international patent specification WO 01/72745, or analogously, for example as described in the Examples.

Compounds of formula XIX and XX are commercially available or may be prepared by known methods.

Where reference is made herein to protected functional groups or to protecting groups, the protecting groups may be chosen in accordance with the nature of the functional group, for example as described in Protective Groups in Organic Synthesis, T. W. Greene and P. G. M. Wuts, John Wiley & Sons Inc, Third Edition, 1999, which reference also describes procedures suitable for replacement of the protecting groups by hydrogen.

Compounds of formula I in free form may be converted into salt form, and vice versa, in a conventional manner. The compounds in free or salt form can be obtained in the form of hydrates or solvates containing a solvent used for crystallization. Compounds of formula I can be recovered from reaction mixtures and purified in a conventional manner. Isomers, such as enantiomers, may be obtained in a conventional manner, e.g. by fractional crystallization or asymmetric synthesis from correspondingly asymmetrically substituted, e.g. optically active, starting materials.

Compounds of formula I and their pharmaceutically acceptable salts, hereinafter referred to alternatively as agents of the invention, are useful as pharmaceuticals. In particular, they exhibit inhibition of phosphatidylinositol 3-kinase (Pi3 kinase) enzymes, especially the gamma isoform (p110γ), which are responsible for generating phosphorylated signalling products. The inhibitory properties of compounds of formula I may be demonstrated in the following test procedures:

Baculovirus expressing different fragments of PI3Kγ fused to GST have been previously described by Stoyanova, S., Bulgarelli-Leva, G., Kirsch, C., Hanck, T., Klinger, R., Wetzker, R., Wymann, M. P. (1997) Lipid- and protein kinase activities of G protein-coupled PI 3-kinase g: structure-activity analysis and interactions with wortmannin. *Biochem. J.*, 324:489. Residues 38-1102 of human PI3Kγ are subcloned into the BamH1 and EcoR1 sites of the transfer vector pAcG2T (Pharmingen) to create a GST-PI3Kγ lacking the first 37 residues of PI3Kγ. To express the recombinant protein, Sf9 (*Spodoptera frugiperda* 9) insect cells are routinely maintained at densities between $3\times10^5$ and $3\times10^6$ cells/ml in serum containing TNMFH medium (Sigma). Sf9 cells, at a density of $2\times10^6$ are infected with human GST-PI3KγΔ34 baculovirus at a multiplicity of infection (m.o.i.) of 1 for 72 hours. The infected cells are harvested by centrifugation at 1400 g for 4 minutes at 4° C. and the cell pellets are frozen at −80° C. Both Sf9 and Sf21 cells work equally well. Sf9 cells ($1\times10^9$) are resuspended in 100 ml cold (4° C.) lysis buffer (50 mM Tris-HCl pH 7.5, 1% Triton X-100, 150 mM NaCl, 1 mM NaF, 2 mM DTT and protease inhibitors. Cells are incubated on ice for 30 minutes then centrifuged at 15000 g for 20 minutes at 4° C. Purification of the supernatant sample is carried out at 4° C. by affinity chromatography using SEPHAROSE™ agarose gel beads coupled to glutathione (from Amersham Pharmacia Biotech). A cell lysate/GST resin ratio of 50:1 is used. The GST resin is firstly pre-rinsed to remove ethanol preservative and then equilibrated with lysis buffer. Cell lysate (supernatant) is added (usually as 50 ml lysate to 1 ml GST resin in 50 ml tubes) and gently rotated on a mixer at 4° C. for 2-3 hours. The unbound flow through sample is collected by centrifugation at 1000 g for 5 minutes at 4° C. using a DENLEY™ centrifuge. The 1 ml GST resin containing bound material is transferred to a 15 ml FALCON™ centrifuge tube for subsequent washing and elution steps. Firstly a series of 3 cycles of washings (mixing by gentle inversion) is performed with 15 ml ice cold wash Buffer A (50 mM Tris-HCl pH 7.5, 1% Triton X-100, 2 mM DTT) interspersed with centrifugation at 1000 g for 5 minutes at 4° C. A final single wash step is performed with 15 ml ice cold wash Buffer B (50 mM Tris-HCl pH 7.5, 2 mM DTT) and then centrifuged at 1000 g for 5 minutes at 4° C. The washed GST resin is finally eluted with 4 cycles of 1 ml ice cold elution buffer (50 mM Tris-HCl pH 7.5, 10 mM reduced glutathione, 2 mM DTT, 150 mM NaCl, 1 mM NaF, 50% ethylene glycol and protease inhibitors) interspersed with centrifugation at 1000 g for 5 minutes at 4° C. Samples are aliquoted and stored at −20° C.

An in vitro kinase assay is established that measures the transfer of the terminal phosphate of adenosine triphosphate to phosphatidylinositol. The kinase reaction is performed in a white 96 well microtitre plate as a Scintillation Proximity Assay. Each well contains 10 µl test compound in 5% dimethylsulphoxide and 20 µl assay mix (40 mM Tris, 200 mM NaCl, 2 mM ethyleneglycol-aminoethyl-tetraacetic acid (EGTA), 15 µg/ml phosphatidylinositol, 12.5 µM adenosine triphosphate (ATP), 25 mM MgCl$_2$, 0.1 µCi [$^{33}$P]ATP). The reaction is started by the addition of 20 µl of enzyme mix (40 mM Tris, 200 mM NaCl, 2 mM EGTA containing recombinant GST-p110γ). The plate is incubated at room temperature for 60 minutes and the reaction terminated by the adding 150 µl of WGA-bead stop solution (40 mM Tris, 200 mM NaCl, 2 mM EGTA, 1.3 mM ethylene diamine tetraacetic acid (EDTA), 2.6 µM ATP and 0.5 mg of Wheat Germ Agglutinin-SPA beads (Amersham Biosciences) to each well. The plate is sealed, incubated at room temperature for 60 minutes, centrifuged at 1200 rpm and then counted for 1 minute using a scintillation counter. Total activity is determined by adding 10 µl of 5% dimethylsulphoxide (DMSO) and non-specific activity is determined by adding 10 µl 50 mM EDTA in place of the test compound.

Compounds of the Examples hereinbelow have IC$_{50}$ values below 0.5 µM in the aforementioned assay. For example the compounds of Examples 1, 6, 11, 17, 22, 27, 33, 56, 67, 82, 91, 108, 120 and 133 have IC$_{50}$ values of 0.075, 0.165, 0.093, 0.106, 0.050, 0.017, 0.073, 0.127, 0.016, 0.164, 0.025, 0.005, 0.008 and 0.057 respectively.

Having regard to their inhibition of phosphatidylinositol 3-kinase enzymes, compounds of formula I in free or pharmaceutically acceptable salt form, hereinafter alternately referred to as "agents of the invention", are useful in the treatment of conditions which are mediated by the activation of the Pi3 kinase enzymes, particularly inflammatory or allergic conditions. Treatment in accordance with the invention may be symptomatic or prophylactic.

Accordingly, agents of the invention are useful in the treatment of inflammatory or obstructive airways diseases, resulting, for example, in reduction of tissue damage, airways inflammation, bronchial hyperreactivity, remodelling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their anti-inflammatory activity, in particular in relation to inhibition of eosinophil activation, agents of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Agents of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin. Treatment in accordance with the invention may be symptomatic or prophylactic.

Agents of the invention may also be used for the treatment of other diseases or conditions, in particular diseases or conditions having an inflammatory component, for example, treatment of diseases and conditions of the eye such as conjunctivitis, keratoconjunctivitis sicca, and vernal conjunctivitis, diseases affecting the nose including allergic rhinitis, and inflammatory disease in which autoimmune reactions are implicated or having an autoimmune component or aetiology, including autoimmune haematological disorders (e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary billiary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy).

Other diseases or conditions which may be treated with agents of the invention include septic shock, rheumatoid arthritis, osteoarthritis, proliferative diseases such as cancer, athersclerosis, allograft rejection following transplantation, stroke, obesity, restenosis, diabetes, e.g. diabetes mellitus type I (juvenile diabetes) and diabetes mellitus type II, diarrheal diseases, ischemia/reperfusion injuries, retinopathy, such as diabetic retinopathy or hyperbaric oxygen-induced retinopathy, and conditions characterised by elevated intraocular pressure or secretion of ocular aqueous humor, such as glaucoma.

The effectiveness of an agent of the invention in inhibiting inflammatory conditions, for example in inflammatory airways diseases, may be demonstrated in an animal model, e.g. a mouse or rat model, of airways inflammation or other inflammatory conditions, for example as described by Szarka et al, *J. Immunol. Methods* (1997) 202:49-57; Renzi et al, *Am. Rev. Respir. Dis.* (1993) 148:932-939; Tsuyuki et al., *J. Clin. Invest.* (1995) 96:2924-2931; and Cernadas et al (1999) *Am. J. Respir. Cell Mol. Biol.* 20:1-8.

The agents of the invention are useful in the manufacture of a medicament for treatment of a disease mediated by phosphatidylinositol 3-kinase. More specifically the agents of the invention are useful in the manufacture of a medicament for treatment of respiratory diseases, allergies, rheumatoid arthritis, osteoarthritis, rheumatic disorders, psoriasis, ulcerative colitis, Crohn's disease, septic shock, proliferative disorders such as cancer, atherosclerosis, allograft rejection following transplantation, diabetes, stroke, obesity or restenosis. Treatment in accordance with the invention may be symptomatic or prophylactic.

The agents of the invention are also useful as co-therapeutic agents for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or antitussive drug substance, said agent of the invention and said drug substance being in the same or different pharmaceutical composition.

Such anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such as those described in U.S. Pat. No. 5,451,700; LTD4 antagonists such as montelukast and zafirlukast; PDE4 inhibitors such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659 (Parke-Davis), AWD-12-281 (Asta Medica), CDC-801 (Celgene), SelCID™ CC-10004 (Celgene), KW-4490 (Kyowa Hakko Kogyo), WO 03/104204, WO 03/104205, WO 04/000814, WO 04/000839 and WO 04005258 (Merck), as well as those described in WO 98/18796 and WO 03/39544; A2a agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; A2b antagonists such as those described in WO 02/42298; and beta-2 adrenoceptor agonists such as albuterol (salbutamol), metaproterenol, terbutaline, salmeterol, fenoterol, procaterol, and especially, formoterol and pharmaceutically acceptable salts thereof, and compounds (in free or salt or solvate form) of formula I of WO 00/75114, which document is incorporated herein by reference, preferably compounds of the Examples thereof, especially a compound of formula

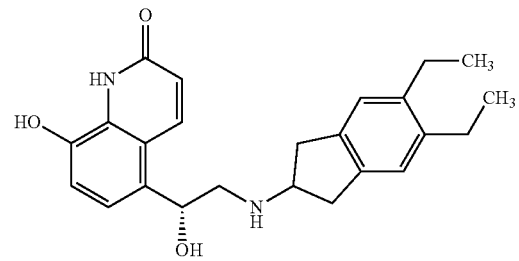 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601.

Such bronchodilatory drugs include anticholinergic or antimuscarinic agents, in particular ipratropium bromide, oxitropium bromide, tiotropium salts and CHF 4226 (Chiesi), but also those described in WO 01/04118, WO 02/51841, WO 02/53564, WO 03/00840, WO 03/87094, WO 04/05285, WO 02/00652, WO 03/53966, EP 424021, U.S. Pat. No. 5,171,744, U.S. Pat. No. 3,714,357 and WO 03/33495.

Such co-therapeutic antihistamine drug substances include cetirizine hydrochloride, acetaminophen, clemastine fumarate, promethazine, loratidine, desloratidine, diphenhydramine and fexofenadine hydrochloride.

Combinations of agents of the invention and steroids, beta-2 agonists, PDE4 inhibitors or LTD4 antagonists may be used, for example, in the treatment of COPD or, particularly, asthma. Combinations of agents of the invention and anticholinergic or antimuscarinic agents, PDE4 inhibitors, dopamine receptor agonists or LTB4 antagonists may be used, for example, in the treatment of asthma or, particularly, COPD.

Other useful combinations of agents of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-aminium chloride (TAK-770), and CCR-5 antagonists described in U.S. Pat. No. 6,166,037 (particularly claims 18 and 19), WO 0066558 (particularly claim 8) and WO 0066559 (particularly claim 9).

The agents of the invention may be administered by any appropriate route, e.g. orally, for example in the form of a tablet or capsule; parenterally, for example intravenously; by inhalation, for example in the treatment of inflammatory or obstructive airways disease; intranasally, for example in the treatment of allergic rhinitis; topically to the skin, for example in the treatment of atopic dermatitis; or rectally, for example in the treatment of inflammatory bowel disease.

The present invention also provides a pharmaceutical composition comprising a compound of formula I in free form or in the form of a pharmaceutically acceptable salt, optionally together with a pharmaceutically acceptable diluent or carrier therefor. The composition may contain a co-therapeutic agent such as an anti-inflammatory, bronchodilatory or antihistamine drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

When the composition comprises an aerosol formulation, it preferably contains, for example, a hydro-fluoro-alkane (HFA) propellant such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents such as lactose. When the composition comprises a dry powder formulation, it preferably contains, for example, the compound of formula I having a particle diameter up to 10 microns, optionally together with a diluent or carrier, such as lactose, of the desired particle size distribution and a compound that helps to protect against product performance deterioration due to moisture. When the composition comprises a nebulised formulation, it preferably contains, for example, the compound of formula I either dissolved, or suspended, in a vehicle containing water, a co-solvent such as ethanol or propylene glycol and a stabiliser, which may be a surfactant.

The invention includes (A) an agent of the invention in inhalable form, e.g. in an aerosol or other atomisable composition or in inhalable particulate, e.g. micronised form, (B) an inhalable medicament comprising an agent of the invention in inhalable form; (C) a pharmaceutical product comprising such an agent of the invention in inhalable form in association with an inhalation device; and (D) an inhalation device containing an agent of the invention in inhalable form.

Dosages of agents of the invention employed in practising the present invention will of course vary depending, for example, on the particular condition to be treated, the effect desired and the mode of administration. In general, suitable daily dosages for oral administration are of the order of 0.1 to 10 mg/kg.

EXAMPLES

Especially preferred compounds of formula I include compounds formula XXI

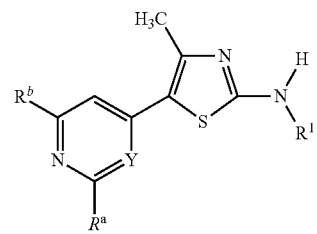

XXI where $R^1$, Y, $R^a$ and $R^b$ are as shown in Table 1 below, the methods of preparation being described thereafter. The table also shows mass spectrometry data. The Examples are in free form.

TABLE I

| Ex. | $R^1$ | Y | $R^a$ | $R^b$ | M/s MH+ |
|---|---|---|---|---|---|
| 1 | ![pyrazine] | C | H | H | 269.9 |
| 2 | ![pyrazine] | C | Cl | H | 304.0 |

TABLE I-continued
| Ex. | R¹ | Y | Rᵃ | Rᵇ | M/s MH+ |
|---|---|---|---|---|---|
| 3 | 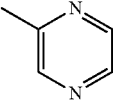 | C | 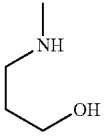 | H | 342.7 |
| 4 | 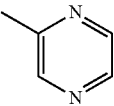 | C | 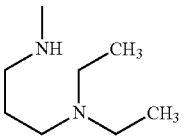 | H | 397.9 |
| 5 | 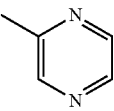 | C | 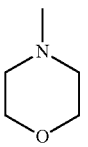 | H | 355.0 |
| 6 | 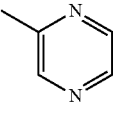 | C | 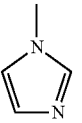 | H | 336.2 |
| 7 | 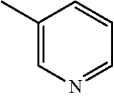 | C | Cl | H | 303.0 |
| 8 | 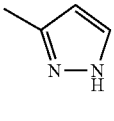 | C | Cl | H | 292.1 |
| 9 | 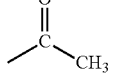 | C | Cl | H | 268 |
| 10 | 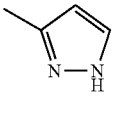 | C | 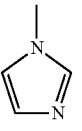 | H | 324.2 |
| 11 | 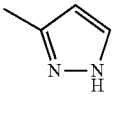 | C | 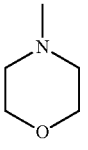 | H | 343.2 |
| 12 | 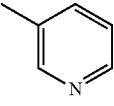 | C | 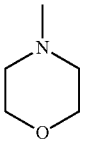 | H | 354 |
| 13 | 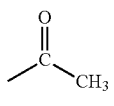 | C | 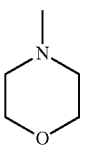 | H | 319.2 |

TABLE I-continued

| Ex. | R¹ | Y | Rª | R^b | M/s MH+ |
|---|---|---|---|---|---|
| 14 | ethyl 3-acetamidopropanoate | C | 4-methylmorpholin-4-yl | H | 420.3 |
| 15 | ethyl 4-acetamidobutanoate | C | 4-methylmorpholin-4-yl | H | 434.3 |
| 16 | ethyl 2-acetamidoacetate | C | H | H | 321 |
| 17 | ethyl 3-acetamidopropanoate | C | H | H | 335.2 |
| 18 | N-methylacetamide | C | H | H | 192.1 |
| 19 | acetone | C | —CH₃ | —CH₃ | 262.2 |
| 20 | N-(2-(5-ethyloxazol-2-yl)ethyl)acetamide | C | —CH₃ | —CH₃ | 386.1 |
| 21 | N-((1-methyl-1H-pyrrol-2-yl)methyl)acetamide | C | H | H | 363.2 |

TABLE I-continued

| Ex. | R¹ | Y | Rᵃ | Rᵇ | M/s MH+ |
|---|---|---|---|---|---|
| 22 | CH₃-C(=O)-NH-CH₂-CH₂-C(=O)-O-C(CH₃)₃ | C | H | H | 328.1 |
| 23 | CH₃-C(=O)-NH-CH₂-CH₂-(5-ethyl-oxazol-2-yl) | C | H | H | 358.1 |
| 24 | CH₃-C(=O)-NH-CH₂-CH₂-C(=O)-N(CH₃)₂ | C | H | H | 334.1 |
| 25 | CH₃-C(=O)- | N | morpholin-4-yl | H | 320.1 |
| 26 | CH₃-C(=O)-NH-CH₂-CH₂-(5-ethyl-oxazol-2-yl) | N | morpholin-4-yl | H | 444.1 |
| 27 | CH₃-C(=O)- | N | cyclopropyl | H | 275.1 |
| 28 | CH₃-C(=O)- | N | isopropyl | H | 277.1 |
| 29 | CH₃-C(=O)- | N | —CH₃ | H | 249.1 |
| 30 | CH₃-C(=O)- | N | pyridin-3-yl | H | 312.1 |

Preparation of Certain Starting Materials 2-(5-Ethyl-oxazol-2-yl)-ethylamine)

a) [2-(2-Hydroxy-butylcarbamoyl)-ethyl]-carbamic acid benzyl ester

A mixture comprising Z-Beta-Ala-OH (9.0 g, 40.3 mmol), EDCI.HCl (10.0 g, 52.4 mmol), hydroxybenzotriazole (5.45 g, 40.3 mmol), triethylamine (7.3 ml, 52.4 mmol) in DCM (150 ml) is stirred at 0° C. for 30 minutes. 1-amino-2-butanol (4.2 ml, 44.3 mmol) is added in one portion and stirring continues for 1 hour. The reaction mixture is diluted with water (150 ml) and extracted with dichloromethane (2×150 ml) The organic layers are combined, dried over MgSO$_4$, filtered and concentrated in vacuo to yield a crude white solid. The product is purified by chromatography on silica eluting with ethanol-ethyl acetate (1:10) to give the titled compound.

b) [2-(2-Oxo-butylcarbamoyl)-ethyl]-carbamic acid benzyl ester

To a stirred solution of oxalyl chloride (2M in DCM) (13.35 ml, 26.5 mmol) in dry DCM at −78° C. is added dropwise DMSO (2.5 ml, 35.4 mmol). After stirring for 15 minutes, the reaction mixture is treated with a solution of [2-(2-Hydroxy-butylcarbamoyl)-ethyl]-carbamic acid benzyl ester (step 1) (6.5 g, 22.1 mol) in dry DCM (40 ml). Triethylamine (13 ml) is added after 1 hour and after stirring at −78° C. for 90 minutes, the reaction mixture is allowed to warm to room temperature. The reaction is diluted with DCM (100 ml) and washed with HCl (1 M, 200 ml), saturated sodium bicarbonate solution (200 ml), water (200 ml) and brine (200 ml). The organic portion is dried over MgSO$_4$, filtered and concentrated in vacuo to yield the titled compound as a white solid.

c) [2-(5-Ethyl-oxazol-2-yl)-ethyl]-carbamic acid benzyl ester

To a stirred suspension of polymer supported triphenylphosphene (19.6 g, 58.9 mmol) in DCM (250 ml) is added iodine (14.95 g, 58.9 mmol). After stirring at room temperature for 10 minutes, the mixture is treated with triethylamine (16.4 ml, 117.5 mmol) followed by a solution of [2-(2-Oxo-butylcarbamoyl)-ethyl]-carbamic acid benzyl ester (Step 2) (6.88 g, 23.5 mmol) in DCM (50 ml). The reaction mixture is stirred overnight and then filtered through Celite™ filter material, washed through with DCM (500 ml) and the solvent removed in vacuo to yield the titled compound as a brown solid.

d) 2-(5-Ethyl-oxazol-2-yl)-ethylamine (hydrochloride salt)

A solution of [2-(5-Ethyl-oxazol-2-yl)-ethyl]-carbamic acid benzyl ester (step 3) (0.41 g, 1.49 mmol), 2M HCl (0.75 ml) in ethanol (40 ml) is stirred under hydrogen in the presence of 10% Pd on Carbon (0.041 g) for 5 hours. The reaction mixture is filtered and concentrated in vacuo to yield the titled compound. This is neutralised using triethylamine to produce 2-(5-ethyl-oxazol-2-yl)-ethylamine 3-Amino-N,N-dimethyl-propionamide a) 3-Amino-N,N-dimethyl-propionamide (2-Dimethylcarbamoyl-ethyl)-carbamic acid benzyl ester To a stirred, cooled (0° C.) solution of Z-Beta-Ala-OH (1.784 g, 8.0 mmol) in dioxane (20 ml) is added EDCI.HCl (2.145 g, 11.2 mmol), hydroxybenzotriazole (1.08 g, 8.0 mmol) and triethylamine (1.56 ml, 11.2 mmol). After stirring at 0° C. for 30 minutes, dimethylamine (0.397 g, 8.8 mmol) is added and stirring continued for a further hour. The reaction mixture was allowed to warm to room temperature and the solvent is removed in vacuo. Initial purification of the crude residue is carried out by flash chromatography of silica eluting with ethyl acetate. The combined organic factions are washed with water (3×20 ml), brine (1×50 ml) and dried over MgSO$_4$. The solvent is removed in vacuo to yield the titled compound as a pale yellow solid.

b) 3-Amino-N,N-dimethyl-propionamide

To a solution of (2-dimethylcarbamoyl-ethyl)-carbamic acid benzyl ester (0.9 g, 3.6 mmol) in ethanol (35 ml) is added 10% Pd on Carbon (0.09 g). The solution was stirred in the presence of a constant flow of hydrogen [in series with a sodium hydroxide (4N) scrub]. The reaction mixture is filtered and concentrated in vacuo to yield the titled compound as a pale yellow oil.

Preparation of Specific Examples

Example 1

(4-Methyl-5-pyridin-4-yl-thiazol-2-yl)-pyrazin-2-yl-amine

1a) Pyrazin-2-yl-thiourea

Aminopyrazine (2 g, 21.03 mmol) is dissolved in ethanol (20 ml) and benzoylisothiocyanate (2.82 ml) is added dropwise. The mixture is heated to 80° C. with stirring for 10 minutes then allowed to cool to room temperature. The solvent is removed in vacuo and the resulting solid dissolved in 1M sodium hydroxide (30 ml) and heated under reflux for 1 hour. The resultant suspension is filtered and the solid washed with water and a little cold methanol. The solid is dried in vacuo to yield the titled compound, m.p. 239-239.5° C., MH$^+$ (AP+): 138 (M$^+$—NH$_3$). Other thioureas used are either commercially available or prepared in an analogous manner from the appropriate starting amine 1b) (4-Methyl-5-pyridin-4-yl-thiazol-2-yl)-pyrazin-2-yl-amine To a stirred solution of 1-pyridin-4-yl-propan-2-one (0.1 g, 0.812 mmol) in dioxane (7 ml) is added bromine (0.029 ml, 0.569 mmol) dropwise. After 45 minutes, the solvent is removed in vacuo and the crude product is dissolved in ethanol (15 ml). The solution is treated with pyrazin-2-yl-thiourea (0.125 g, 0.812 mmol) and the reaction mixture is heated at 60° C. for 3 hours. The solvent is removed in vacuo and purification by chromatography on silica, eluting with ethyl acetate-methanol affords the titled compound.

Example 2

[5-(2-Chloro-pyridin-4-yl)-4-methyl-thiazol-2-yl]-pyrazin-2-yl-amine 2a) 1-(2-Chloro-pyridin-4-yl)-propan-2-one To a stirred solution of diisopropylamine (14.22 ml, 101.43 mmol) cooled to −78° C. is added dropwise butyllithium (60 ml). The reaction mixture is stirred and allowed to warm to 0°

C. over 15 minutes after which time 2-chloro-4-methylpyridine is added to the stirred solution. After 1 hour, ethyl acetate (18.88 ml) and THF (78 ml) are added over 45 minutes followed by acetic acid (11.4 ml, 193.2 mmol) and stirring continued for 20 minutes. The reaction mixture is concentrated in vacuo and the crude product dissolved in with water (200 ml). The aqueous is extracted with chloroform (3×300 ml) and the combined organic portions washed with water (200 ml), brine (200 ml), dried over $MgSO_4$ and the solvent removed in vacuo to yield the crude product as a brown oil. Purification by chromatography on silica, eluting with ethyl acetate-hexane affords the titled compound.

2b) [5-(2-Chloro-pyridin-4-yl)-4-methyl-thiazol-2-yl]-pyrazin-2-yl-amine

The titled compound is prepared by an analogous procedure to (4-Methyl-5-pyridin-4-yl-thiazol-2-yl)-pyrazin-2-yl-amine (Example 1) by replacing 1-pyridin-4-yl-propan-2-one (1b) in this procedure with 1-(2-chloro-pyridin-4-yl)-propan-2-one.

Example 3

3-{4-[4-Methyl-2-(pyrazin-2-ylamino)-thiazol-5-yl]-pyridin-2-ylamino}-propan-1-ol

[5-(2-Chloro-pyridin-4-yl)-4-methyl-thiazol-2-yl]-pyrazin-2-yl-amine (Example 2b, 0.077 g, 0.254 mmol) is suspended in 3-amino-propanol (3 ml) and heated to 150° C. using microwave heating (Prolabo Synthewave™ s402 microwave oven). After 1 hour, the reaction mixture is concentrated in vacuo and diluted with water (50 ml). The aqueous is extracted with ethyl acetate (2×100 ml). The combined organic extract is dried ($MgSO_4$) and concentrated to afford the titled compound which is purified by filtration and recrystallised from dichloromethane.

Example 4

N,N-Diethyl-N'-{4-[4-methyl-2-(pyrazin-2-ylamino)-thiazol-5-yl]-pyridin-2-yl}-propane-1,3-diamine The titled compound is prepared following the same route as Example 3 by replacing 3-amino-propanol with N,N-diethylpropylamine

Example 5

[4-Methyl-5-(2-morpholin-4-yl-pyridin-4-yl)-thiazol-2-yl]-pyrazin-2-yl-amine This compound is prepared following the same route as Example 3 by replacing 3-amino-propanol with morpholine.

Example 6

[5-(2-Imidazol-1-yl-pyridin-4-yl)-4-methyl-thiazol-2-yl]-pyrazin-2-yl-amine

A stirred solution of [5-(2-Chloro-pyridin-4-yl)-4-methyl-thiazol-2-yl]-pyrazin-2-yl-amine (Ex. 2b, 0.4 g, 1.32 mmol) in DMSO (10 ml) is treated with imidazole (0.18 g, 2.64 mmol) followed by caesium carbonate (0.86 g, 2.64 mmol). The reaction mixture is heated to 140° C. for 48 hours and then allowed to cool to room temperature. The mixture is diluted with water (100 ml) and extracted with ethyl acetate (4×100 ml). The organics are combined, dried over $MgSO_4$ and the solvent removed in vacuo to yield the crude product as a yellow oil. Purification by chromatography on silica, eluting with ethyl acetate-methanol (9:1) affords the titled compound.

Examples 7 to 9

These compounds, namely [5-(2-Chloro-pyridin-4-yl)-4-methyl-thiazol-2-yl]-pyridin-3-yl-amine, [5-(2-Chloro-pyridin-4-yl)-4-methyl-thiazol-2-yl]-(1H-pyrazol-3-yl)-amine and N-[5-(2-Chloro-pyridin-4-yl)-4-methyl-thiazol-2-yl]-acetamide respectively, are prepared using the procedure of Example 2 from 1-(2-Chloro-pyridin-4-yl)-propan-2-one and the appropriate thiourea.

Example 10

[5-(2-Imidazol-1-yl-pyridin-4-yl)-4-methyl-thiazol-2-yl]-(1H-pyrazol-3-yl)-amine This compound is prepared following the same route as Example 6 by replacing [5-(2-Chloro-pyridin-4-yl)-4-methyl-thiazol-2-yl]-pyrazin-2-yl-amine (Example 2) with [5-(2-Chloro-pyridin-4-yl)-4-methyl-thiazol-2-yl]-(1H-pyrazol-3-yl)-amine (Example 8).

Example 11

[4-Methyl-5-(2-morpholin-4-yl-pyridin-4-yl)-thiazol-2-yl]-(1H-pyrazol-3-yl)-amine This compound is prepared following the same route as Example 5 by replacing [5-(2-Chloro-pyridin-4-yl)-4-methyl-thiazol-2-yl]-pyrazin-2-yl-amine (Example 2) with [5-(2-Chloro-pyridin-4-yl)-4-methyl-thiazol-2-yl]-(1H-pyrazol-3-yl)-amine (Example 8).

Example 12

[4-Methyl-5-(2-morpholin-4-yl-pyridin-4-yl)-thiazol-2-yl]-pyridin-3-yl-amine This compound is prepared following the same route as Example 5 by replacing [5-(2-Chloro-pyridin-4-yl)-4-methyl-thiazol-2-yl]-pyrazin-2-yl-amine (Example 2) with [5-(2-Chloro-pyridin-4-yl)-4-methyl-thiazol-2-yl]-pyridin-3-yl-amine (Example 7).

Example 13

N-[4-Methyl-5-(2-morpholin-4-yl-pyridin-4-yl)-thiazol-2-yl]-acetamide

13a) 1-(2-Morpholin-4-yl-pyridin-4-yl)-propan-2-one

A stirred solution of 1-(2-chloro-pyridin-4-yl)-propan-2-one (1.6 g, 9.47 mmol) in morpholine is heated to 105° C. for 3 days. The morpholine is removed in vacuo to yield the crude product. Purification by chromatography on silica, eluting with 1:1 ethyl acetate-hexane affords the title compound.

13b) 4-Methyl-5-(2-morpholin-4-yl-pyridin-4-yl)-thiazol-2-ylamine hydrobromide The titled compound is prepared by an analogous procedure to (4-methyl-5-pyridin-4-yl-thiazol-2-yl)-pyrazin-2-ylamine (Example 1) by replacing 1-pyridin-4-yl-propan-2-one (1b) with 1-(2-morpholin-4-yl-pyridin-4-yl)-propan-2-one (13a) and pyrazin-2-yl-thiourea (1a) with N-acetylthiourea.

13c) N-[4-Methyl-5-(2-morpholin-4-yl-pyridin-4-yl)-thiazol-2-yl]-acetamide

A stirred suspension of 4-methyl-5-(2-morpholin-4-yl-pyridin-4-yl)-thiazol-2-ylamine hydrobromide (13b) (0.035 g, 0.098 mmol) and ethyldiisopropylamine (0.034 ml, 0.196 mmol) in acetic anhydride (2 ml) is heated to 75° C. for 2 hours. The reaction mixture is cooled to room temperature and the solvent is removed in vacuo. Ethyl acetate is added and a white solid by-product is filtered off. The filtrate is concentrated in vacuo to afford the titled compound as a white solid.

Example 14

3-{3-[4-Methyl-5-(2-morpholin-4-yl-pyridin-4-yl)-thiazol-2-yl]-ureido}-propionic acid ethyl ester To a stirred suspension of 4-Methyl-5-(2-morpholin-4-yl-pyridin-4-yl)-thiazol-2-ylamine hydrobromide (13b) (0.04 g, 0.112 mmol) in DCM (3 ml) is added ethyldiisopropylamine (0.039 ml, 0.224 mmol) to afford a solution. The reaction mixture is then treated with ethyl 3-isocyanatopropionate (0.015 ml, 0.112 mmol) and heated whilst stirring to 60° C. for 5 hours in a sealed reaction vessel. The solution is diluted with DCM and hydrochloric acid (30 ml, 1N HCl) and the layers separated. The aqueous is adjusted to pH 8/9 and extracted with ethyl acetate (3×25 ml). The organics are combined and dried (MgSO$_4$), filtered and concentrated in vacuo to yield a clear oil. Trituration with ether yields the titled compound as a white solid.

Example 15

4-{3-[4-Methyl-5-(2-morpholin-4-yl-pyridin-4-yl)-thiazol-2-yl]-ureido}-butyric acid ethyl ester The titled compound is prepared by an analogous procedure to 3-{3-[4-Methyl-5-(2-morpholin-4-yl-pyridin-4-yl)-thiazol-2-yl]-ureido}-propionic acid ethyl ester (Example 14) by replacing ethyl 3-isocyanatopropionate with 4-isocyanato-butyric acid ethyl ester.

Example 16

[3-(4-Methyl-5-pyridin-4-yl-thiazol-2-yl)-ureido]-acetic acid ethyl ester

A stirred solution of 4-methyl-5-pyridin-4-yl-thiazol-2-ylamine (prepared according to the method described in European patent specification EP 117082 A2) (0.068 g, 3.56 mmol) in DMF (5 ml) is treated with ethyl isocyanatoacetate (0.043 ml, 3.916 mmol) and the solution is stirred overnight. The solvent is removed in vacuo and the crude product is partitioned between ethyl acetate (50 ml) and water (50 ml). The layers are separated and the aqueous portion is extracted with ethyl acetate (2×50 ml). The combined organic portions are washed with water, dried (MgSO$_4$), filtered and concentrated in vacuo to yield an oil. Trituration with ethyl acetate yields the titled compound.

Example 17

3-[3-(4-Methyl-5-pyridin-4-yl-thiazol-2-yl)-ureido]-propionic acid ethyl ester This compound is prepared by an analogous procedure to 3-{3-[4-Methyl-5-(2-morpholin-4-yl-pyridin-4-yl)-thiazol-2-yl]-ureido}-propionic acid ethyl ester (Example 14) by replacing 4-Methyl-5-(2-morpholin-4-yl-pyridin-4-yl)-thiazol-2-ylamine hydrobromide (13b) with 4-methyl-5-pyridin-4-yl-thiazol-2-ylamine (see Example 16 for reference).

Example 18

1-Methyl-3-(4-methyl-5-pyridin-4-yl-thiazol-2-yl)-urea

18a) Imidazole-1-carboxylic acid (4-methyl-5-pyridin-4-yl-thiazol-2-yl)-amide To a stirred solution of carbonyldiimidazole (3.91 g, 24.2 mmol) in DCM (150 ml) is added 4-methyl-5-pyridin-4-yl-thiazol-2-ylamine (prepared according to the method described in EP 117082 A2) (3.08 g, 16.1 mmol) in one portion. The suspension is stirred for 2.5 hours at 40° C. and the reaction mixture is then filtered and washed with DCM to afford the titled compound as a solid.

18b) 1-Methyl-3-(4-methyl-5-pyridin-4-yl-thiazol-2-yl)-urea

Methylamine (0.030 ml of a 40% w/w/solution in water, 0.351 mmol) is added to a stirred suspension of imidazole-1-carboxylic acid (4-methyl-5-pyridin-4-yl-thiazol-2-yl)-amide (18a) (0.1 g, 0.351 mmol) in DMF (3 ml). The reaction mixture is stirred at room temperature for 1 hour and then the solvent is removed in vacuo. The crude product is dissolved in THF/DMF (10:1, 3 ml) and passed through a polymer supported isocyanate resin (0.9 g, 1.1 mmol/g loading) and washed through with THF. The solution is concentrated in vacuo and the residue washed with ethyl acetate and methanol to afford the titled compound.

Example 19

N-[5-(2,6-Dimethyl-pyridin-4-yl)-4-methyl-thiazol-2-yl]-acetamide

The titled compound is prepared by an analogous procedure to (4-Methyl-5-pyridin-4-yl-thiazol-2-yl)-pyrazin-2-yl-amine (Example 1) by replacing 1-pyridin-4-yl-propan-2-one (1b) in this procedure with 1-(2,6-dimethyl-pyridin-4-yl)-propan-2-one and by replacing and pyrazin-2-yl-thiourea (1a) with N-acetylthiourea. 1-(2,6-dimethyl-pyridin-4-yl)-propan-2-one was prepared according to a method described in Tetrahedron Letters, Vol. 25, No. 5, pp 515-518, 1984. (Authors: Claude Erre et al.)

Example 20

1-[5-(2,6-Dimethyl-pyridin-4-yl)-4-methyl-thiazol-2-yl]-3-[2-(5-ethyl-oxazol-2-yl)-ethyl]-urea

20a) 5-(2,6-Dimethyl-pyridin-4-yl)-4-methyl-thiazol-2-ylamine hydrobromide

To a stirred solution of 1-(2,6-dimethyl-pyridin-4-yl)-propan-2-one (0.8 g, 4.9 mmol) in dioxane (20 ml) cooled to 5-10° C. is added dropwise bromine (0.25 ml, 4.9 mmol) in DCM (1 ml). After addition is complete, the reaction mixture is concentrated in vacuo and the crude is dissolved in ethanol (20 ml). The solution is treated with thiourea (0.373 g, 0.4.9 mmol) and the reaction mixture is heated at 60° C. for 30 minutes. The mixture is filtered and the yellow precipitate is washed with ethanol, diethyl ether and dried in vacuo to yield the titled compound.

20b) 5-(2,6-Dimethyl-pyridin-4-yl)-4-methyl-thiazol-2-ylamine

To a stirred solution of 5-(2,6-Dimethyl-pyridin-4-yl)-4-methyl-thiazol-2-ylamine hydrobromide (3.29 g, 11 mmol) in methanol (30 ml) is added sodium methoxide (2 ml of a 30% solution in methanol, 11 mmol). The resulting mixture is filtered through Celite™ filter material and concentrated in vacuo to yield the titled compound.

20c) Imidazole-1-carboxylic acid [5-(2,6-dimethyl-pyridin-4-yl)-4-methyl-thiazol-2-yl]-amide The titled compound is prepared by an analogous procedure to imidazole-1-carboxylic acid (4-methyl-5-pyridin-4-yl-thiazol-2-yl)-amide (example 18a) by replacing 4-methyl-5-pyridin-4-yl-thiazol-2-ylamine with 5-(2,6-Dimethyl-pyridin-4-yl)-4-methyl-thiazol-2-ylamine.

20d) 1-[5-(2,6-Dimethyl-pyridin-4-yl)-4-methyl-thiazol-2-yl]-3-[2-(5-ethyl-oxazol-2-yl)-ethyl]-urea The titled compound is prepared by an analogous procedure to 1-methyl-3-(4-methyl-5-pyridin-4-yl-thiazol-2-yl)-urea (example 18b) by replacing imidazole-1-carboxylic acid (4-methyl-5-pyridin-4-yl-thiazol-2-yl)-amide (example 18a) with imidazole-1-carboxylic acid [5-(2,6-dimethyl-pyridin-4-yl)-4-methyl-thiazol-2-yl]-amide and by replacing methylamine with 2-(5-ethyl-oxazol-2-yl)-ethylamine. The preparation of 2-(5-ethyl-oxazol-2-yl)-ethylamine is described previously.

Examples 21 to 23

These compounds namely, 1-(4-methyl-5-pyridin-4-yl-thiazol-2-yl)-3-(1-methyl-1H-pyrrol-2-ylmethyl)-urea, 3-[3-(4-methyl-5-pyridin-4-yl-thiazol-2-yl)-ureido]-propionic acid tert-butyl ester and 1-[2-(5-ethyl-oxazol-2-yl)-ethyl]-3-(4-methyl-5-pyridin-4-yl-thiazol-2-yl)-urea, are prepared by the same procedure as example 18 replacing methylamine (part 18b) in this example with the appropriate amine.

Example 24

N,N-Dimethyl-3-[3-(4-methyl-5-pyridin-4-yl-thiazol-2-yl)-ureido]-propionamide

To a stirred suspension of imidazole-1-carboxylic acid (4-methyl-5-pyridin-4-yl-thiazol-2-yl)-amide (example 18a) (0.15 g, 0.526 mmol) in dioxane (10 ml) is added 3-amino-N,N-dimethyl-propionamide (0.046 g, 0.526 mmol) in one portion. The reaction mixture is heated to reflux for 2 hours. The reaction mixture is allowed to cool to room temperature and the solvent is removed in vacuo. Trituration with ether/ethyl acetate yields the titled compound as a pale yellow solid.

Example 25

N-[4-Methyl-5-(2-morpholin-4-yl-pyrimidin-4-yl)-thiazol-2-yl]-acetamide a) 1-[2-(4-Methoxy-benzylamino)-4-methyl-thiazol-5-yl]-ethanone

A stirred suspension of 3-chloro, 2,4-pentanedione (1.0 g, 7.43 mmol) and 1-(4-methoxy benzyl)-2-thiourea (1.46 g, 7.43 mmol) in methanol (10 ml) is treated with pyridine (0.6 ml). The reaction mixture is stirred at room temperature for 2 hours and then the solvent is removed in vacuo. The crude residue is triturated with ether to yield the titled compound as a white solid.

b) (E)-3-Dimethylamino-1-[2-(4-methoxy-benzylamino)-4-methyl-thiazol-5-yl]-propenone A stirred suspension of 1-[2-(4-Methoxy-benzylamino)-4-methyl-thiazol-5-yl]-ethanone (25a)(1.0 g, 3.62 mmol) in DMF:DMA (10 ml) is heated to 100° C. overnight. The reaction mixture is concentrated in vacuo to yield a brown oil, which following trituration with ethyl acetate affords the titled compound as an orange solid.

c) (4-Methoxy-benzyl)-[4-methyl-5-(2-morpholin-4-yl-pyrimidin-4-yl)-thiazol-2-yl]-amine To a stirred suspension of (E)-3-dimethylamino-1-[2-(4-methoxy-benzylamino)-4-methyl-thiazol-5-yl]-propenone (25b) (0.585 g, 1.77 mmol) and morpholinoformamidine hydrobromide (0.557 g, 2.65 mmol) in 2-methoxyethanol (10 ml) is added sodium hydroxide (0.142 g, 3.54 mmol). The reaction mixture is stirred and heated to 115° C. for 12 hours. The solvent is removed in vacuo and triturated with ethyl acetate to afford a pale orange solid. Further purification by chromatography on silica eluting with ethyl acetate-hexane (1:1) yields the titled compound.

d) 4-Methyl-5-(2-morpholin-4-yl-pyrimidin-4-yl)-thiazol-2-ylamine

A solution comprising (4-methoxy-benzyl)-[4-methyl-5-(2-morpholin-4-yl-pyrimidin-4-yl)-thiazol-2-yl]-amine (25c) (0.45 g, 1.13 mmol) in trifluoroacetic acid:water (95:5) (10 ml) is heated at 75° C. for days. The solvent is removed in vacuo and the crude residue is dissolved in ethyl acetate. The pH is adjusted to pH12 using 2N sodium hydroxide and the layers are separated. The aqueous layer is extracted with ethyl acetate (2×30 ml). The organic portions are combined and washed with brine (50 ml), dried over MgSO$_4$ and concentrated in vacuo to yield the titled compound as a brown solid.

e) N-[4-Methyl-5-(2-morpholin-4-yl-pyrimidin-4-yl)-thiazol-2-yl]-acetamide

Acetic anhydride (3 ml) is added to 4-methyl-5-(2-morpholin-4-yl-pyrimidin-4-yl)-thiazol-2-ylamine (25d)(0.045 g, 0.162 mmol) and the reaction mixture is heated to 60° C. for 1 hour. The solvent is removed in vacuo and the crude residue is dissolved in ethyl acetate (50 ml) and water (50 ml) The layers are separated and the organic layer is washed with sodium carbonate solution, brine, dried over MgSO$_4$ and concentrated in vacuo to yield a brown oil. The crude residue is purified by chromatography on silica eluting with ethyl acetate-hexane (3:2) to afford the titled compound.

Example 26

1-[2-(5-Ethyl-oxazol-2-yl)-ethyl]-3-[4-methyl-5-(2-morpholin-4-yl-pyrimidin-4-yl)-thiazol-2-yl]-urea a) Imidazole-1-carboxylic acid [4-methyl-5-(2-morpholin-4-yl-pyrimidin-4-yl)-thiazol-2-yl]-amide The titled compound is prepared by an analogous procedure to imidazole-1-carboxylic acid (4-methyl-5-pyridin-4-yl-thiazol-2-yl)-amide (example 18a) by replacing 4-methyl-5-pyridin-4-yl-thiazol-2-ylamine (see example 16 for reference) with 4-methyl-5-(2-morpholin-4-yl-pyrimidin-4-yl)-thiazol-2-ylamine (25d).

b) 1-[2-(5-Ethyl-oxazol-2-yl)-ethyl]-3-[4-methyl-5-(2-morpholin-4-yl-pyrimidin-4-yl)-thiazol-2-yl]-urea The titled compound is prepared by an analogous procedure to 1-methyl-3-(4-methyl-5-pyridin-4-yl-thiazol-2-yl)-urea (example 18b) by replacing imidazole-1-carboxylic acid (4-methyl-5-pyridin-4-yl-thiazol-2-yl)-amide (example 18a) with imidazole-1-carboxylic acid [4-methyl-5-(2-morpholin-4-yl-pyrimidin-4-yl)-thiazol-2-yl]-amide (26a) and by replacing methylamine with 2-(5-ethyl-oxazol-2-yl)-ethylamine. The preparation of 2-(5-ethyl-oxazol-2-yl)-ethylamine is described in example 20d steps 1-4.

Example 27

N-[5-(2-Cyclopropyl-pyrimidin-4-yl)-4-methyl-thiazol-2-yl]-acetamide

The titled compound is prepared by an analogous procedure to N-[4-Methyl-5-(2-morpholin-4-yl-pyrimidin-4-yl)-thiazol-2-yl]-acetamide (25e) by replacing morpholinoformamidine hydrobromide (part 25c) with cyclopropanecarboxamidine hydrochloride.

Example 28

N-[5-(2-Isopropyl-pyrimidin-4-yl)-4-methyl-thiazol-2-yl]-acetamide

The titled compound is prepared by an analogous procedure to N-[4-Methyl-5-(2-morpholin-4-yl-pyrimidin-4-yl)-thiazol-2-yl]-acetamide (25e) by replacing morpholinoformamidine hydrobromide (part 25c) with isobutyramidine hydrochloride.

Example 29

N-[4-Methyl-5-(2-methyl-pyrimidin-4-yl)-thiazol-2-yl]-acetamide

The titled compound is prepared by an analogous procedure to N-[4-Methyl-5-(2-morpholin-4-yl-pyrimidin-4-yl)-thiazol-2-yl]-acetamide (25e) by replacing morpholinoformamidine hydrobromide (part 25c) with acetamidine hydrochloride.

Example 30

N-[4-Methyl-5-(2-pyridin-3-yl-pyrimidin-4-yl)-thiazol-2-yl]-acetamide

The titled compound is prepared by an analogous procedure to N-[4-Methyl-5-(2-morpholin-4-yl-pyrimidin-4-yl)-thiazol-2-yl]-acetamide (25e) by replacing morpholinoformamidine hydrobromide (part 25c) with nicotinamidine hydrochloride.

Especially preferred compounds of formula I also include compounds of formula XXI where $R^1$, Y, $R^a$ and $R^b$ are as shown in Table 2 below, the methods of preparation being described thereafter. The table also shows mass spectrometry data. The Examples are in free form.

TABLE 2

| Ex. | $R^1$ | Y | $R^a$ | $R^b$ | M/s MH+ |
|---|---|---|---|---|---|
| 31 | (structure) | C | —CH$_3$ | —CH$_3$ | 362.2 |
| 32 | (structure) | C | —CH$_3$ | —CH$_3$ | 348.2 |
| 33 | (structure) | C | Cl | H | 392.1 |

TABLE 2-continued
| Ex. | R¹ | Y | Rᵃ | Rᵇ | M/s MH+ |
|---|---|---|---|---|---|
| 34 | 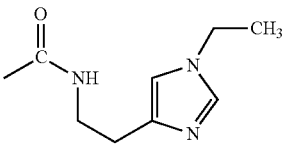 | C | Cl | H | 391.0 |
| 35 | 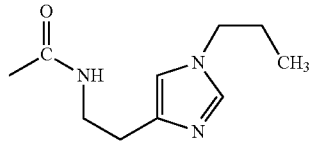 | C | Cl | H | 405.1 |
| 36 | 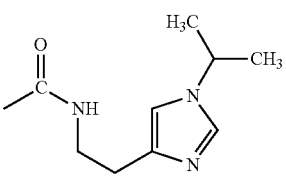 | C | Cl | H | 278.0 |
| 37 | 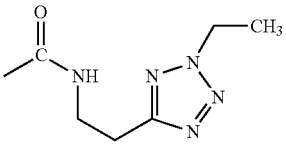 | C | Cl | H | 393.2 |
| 38 | 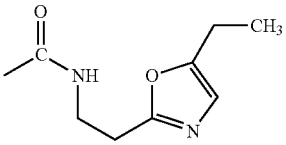 | N |  | —CH₃ | 419.2 |
| 39 | 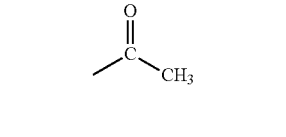 | N | 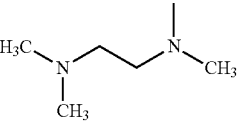 | —CH₃ | 349.2 |
| 40 | 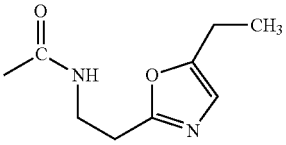 | N | 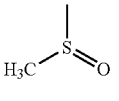 | —CH₃ | 435.1 |
| 41 | 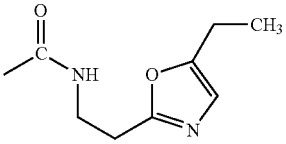 | N | 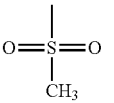 | —CH₃ | 451.2 |
| 42 | 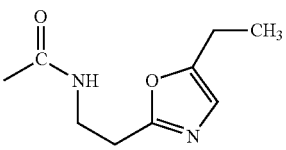 | N | 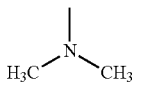 | —CH₃ | 416.2 |

TABLE 2-continued

| Ex. | R¹ | Y | Rᵃ | Rᵇ | M/s MH+ |
|---|---|---|---|---|---|
| 43 | acetamido-ethyl-(5-ethyl-oxazol-2-yl) | N | (CH₃)₂N-CH₂CH₂-N(CH₃)₂ | —CH₃ | 473.3 |
| 44 | acetamido-ethyl-(5-ethyl-oxazol-2-yl) | N | 1-methylimidazole | —CH₃ | 439.9 |
| 45 | acetamido-ethyl-(5-ethyl-oxazol-2-yl) | N | morpholino-ethyl-NHCH₃ | —CH₃ | 501.2 |
| 46 | acetamido-ethyl-(5-ethyl-oxazol-2-yl) | N | (CH₃)₂N-CH₂CH₂-N(CH₃)(C₂H₅) | —CH₃ | 487.3 |
| 47 | acetamido-ethyl-(5-ethyl-oxazol-2-yl) | N | (C₂H₅)₂N-CH₂CH₂-N(CH₃)₂ | —CH₃ | 501.2 |
| 48 | acetamido-ethyl-(5-ethyl-oxazol-2-yl) | N | (CH₃)₂N-CH₂CH₂CH₂-NHCH₃ | —CH₃ | 473.3 |
| 49 | acetamido-ethyl-(5-ethyl-oxazol-2-yl) | N | 1-(3-methylaminopropyl)imidazole | —CH₃ | 496.2 |
| 50 | acetamido-ethyl-(5-ethyl-oxazol-2-yl) | N | (CH₃)₂N-CH₂CH₂CH₂-N(CH₃)₂ | —CH₃ | 487.2 |
| 51 | acetamido-ethyl-(5-ethyl-oxazol-2-yl) | N | (C₂H₅)₂N-CH₂CH₂-NHCH₃ | —CH₃ | 487.2 |

TABLE 2-continued

| Ex. | R¹ | Y | Rᵃ | Rᵇ | M/s MH+ |
|---|---|---|---|---|---|
| 52 | acetamido-ethyl-(5-ethyl-oxazol-2-yl) | N | 3-(dimethylamino)propylamine | —CH₃ | 459.2 |
| 53 | acetamido-ethyl-(5-ethyl-oxazol-2-yl) | N | 1-(3-methylaminopropyl)-4-methylpiperazine | —CH₃ | 528.3 |
| 54 | acetamido-ethyl-(5-ethyl-oxazol-2-yl) | N | 2-morpholino-N,N-dimethylethylamine | —CH₃ | 515.2 |
| 55 | acetamido-ethyl-(5-ethyl-oxazol-2-yl) | N | (pyrrolidin-2-yl)methylamine N-methyl | —CH₃ | 471.3 |
| 56 | acetamido-ethyl-(5-ethyl-oxazol-2-yl) | N | methoxymethyl | —CH₃ | 403.2 |
| 57 | acetamido-ethyl-(5-ethyl-oxazol-2-yl) | N | 4-(2-methoxyethyl)morpholine | —CH₃ | 502.2 |
| 58 | acetamido-ethyl-(1-ethyl-imidazol-4-yl) | N | methylsulfinylmethyl | —CH₃ | 434.2 |
| 59 | acetamido-ethyl-(1-ethyl-imidazol-4-yl) | N | N,N,N',N'-tetramethylethylenediamine | —CH₃ | 472.3 |
| 60 | acetamido-ethyl-(1-propyl-imidazol-4-yl) | N | N,N,N',N'-tetramethylethylenediamine | —CH₃ | 486.3 |

TABLE 2-continued

| Ex. | R¹ | Y | Rᵃ | Rᵇ | M/s MH+ |
|---|---|---|---|---|---|
| 61 | | N | | —CH₃ | 486.3 |
| 62 | | N | | —CH₃ | 411.2 |
| 63 | | N | | —CH₃ | 436.1 |
| 64 | | N | | —CH₃ | 417.2 |
| 65 | | N | | —CH₃ | 474.2 |
| 66 | | N | | —CH₃ | 381.1 |
| 67 | | N | | —CH₃ | 398.1 |
| 68 | | N | | —CH₃ | 436.2 |
| 69 | | N | | H | 459.2 |

TABLE 2-continued
| Ex. | R¹ | Y | Rᵃ | Rᵇ | M/s MH+ |
|---|---|---|---|---|---|
| 70 | 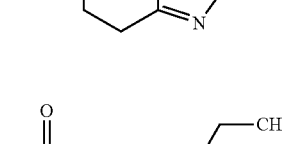 | N | 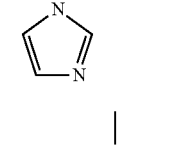 | H | 482.2 |
| 71 | 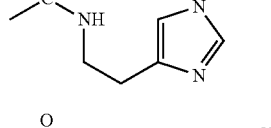 | N | 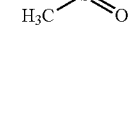 | H | 482.2 |
| 72 | 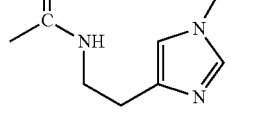 | N | 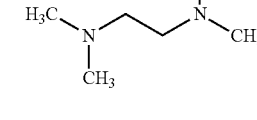 | H | 458.3 |
| 73 | 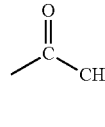 | N | 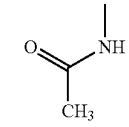 | H | 292.1 |
| 74 | 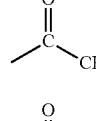 | N | 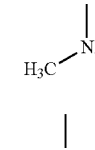 | H | 264.1 |
| 75 | 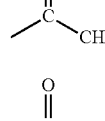 | N | 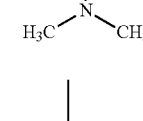 | H | 278.1 |
| 76 |  | N | 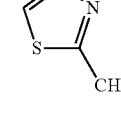 | H | 332.1 |
| 77 | 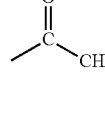 | N | 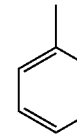 | H | 311.2 |
| 78 | 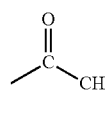 | N | 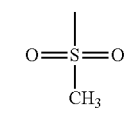 | H | 313.1 |
| 79 | 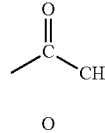 | N | 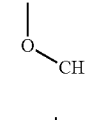 | H | 265.1 |
| 80 | 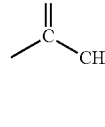 | N | 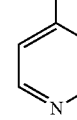 | H | 312.1 |

TABLE 2-continued

| Ex. | R¹ | Y | Rᵃ | Rᵇ | M/s MH+ |
|---|---|---|---|---|---|
| 81 | acetyl (CH₃COCH₂-) | N | 2-pyridyl | H | 312.1 |
| 82 | CH₃C(O)NH-CH₂CH₂-C(O)O-C(CH₃)₃ | N | cyclopropyl | H | 404.2 |
| 83 | CH₃C(O)NH-CH₂CH₂-(5-ethyl-oxazol-2-yl) | N | cyclopropyl | H | 399.2 |
| 84 | CH₃C(O)NH-CH₂CH₂-C(O)O-C(CH₃)₃ | N | N(CH₃)₂ | H | 407.2 |
| 85 | CH₃C(O)NH-CH₂CH₂-(5-ethyl-oxazol-2-yl) | N | N(CH₃)₂ | H | 402.2 |
| 86 | CH₃C(O)NH-CH₂CH₂-(3-ethyl-1,2,4-oxadiazol-5-yl) | N | N(CH₃)₂ | H | 403.2 |
| 87 | CH₃COCH₃ (acetone-like) | N | —CH₃ | —CH₃ | 262.3 |
| 88 | CH₃C(O)NH-CH₂CH₂-(5-ethyl-oxazol-2-yl) | N | —CH₃ | —CH₃ | 387.1 |
| 89 | CH₃C(O)NH-CH₂CH₂-(1-ethyl-imidazol-4-yl) | N | —CH₃ | —CH₃ | 386.2 |

TABLE 2-continued

| Ex. | R¹ | Y | Rᵃ | Rᵇ | M/s MH+ |
|---|---|---|---|---|---|
| 90 | (acetamido-ethyl)-(1-propyl-imidazole) | N | —CH₃ | —CH₃ | 400.3 |
| 91 | H | N | tert-butyl | H | 249.1 |
| 92 | acetyl | N | tert-butyl | H | 291.2 |
| 93 | ethyl 4-oxopentanoate | N | tert-butyl | H | 390.5 |
| 94 | (dimethylamino)acetyl | N | tert-butyl | H | 334.2 |
| 95 | 2,5-dioxohexyl | N | tert-butyl | H | 347.2 |
| 96 | 2,6-dioxooctyl | N | tert-butyl | H | 361.2 |
| 97 | (acetamido-ethyl)-(3-ethyl-1,2,4-oxadiazole) | N | tert-butyl | H | 414.2 |
| 98 | ethyl 4-acetamidobutanoate | N | tert-butyl | H | 406.2 |
| 99 | N-(2-propoxyethyl)acetamide | N | tert-butyl | H | 378.2 |
| 100 | N-acetyl-glycyl-N,N-dimethyl | N | tert-butyl | H | 377.2 |
| 101 | N-acetyl-β-alanyl-(2-hydroxy-1,1-dimethylethyl)amide | N | tert-butyl | H | 435.2 |

TABLE 2-continued

| Ex. | R¹ | Y | Rᵃ | Rᵇ | M/s MH+ |
|---|---|---|---|---|---|
| 102 | H₃C-C(=O)-NH-CH₂CH₂-CH(OEt)₂ | N | C(CH₃)₃ | H | 422.2 |
| 103 | H₃C-C(=O)-NH-CH₂CH₂-C(=O)-O-CH₂CH₃ | N | C(CH₃)₃ | H | 377.2 |
| 104 | H₃C-C(=O)-NH-CH₂CH₂CH₂-OH | N | C(CH₃)₃ | H | 350.2 |
| 105 | H₃C-C(=O)-NH-CH₂-(2-pyridyl) | N | C(CH₃)₃ | H | 383.2 |
| 106 | H₃C-C(=O)-NH-CH₂-(3-pyridyl) | N | C(CH₃)₃ | H | 383.2 |
| 107 | H₃C-C(=O)-NH-CH₂-(4-pyridyl) | N | C(CH₃)₃ | H | 383.2 |
| 108 | H₃C-C(=O)-NH-CH₂CH₂-O-CH₃ | N | C(CH₃)₃ | H | 350.2 |
| 109 | H₃C-C(=O)-NH-CH₂CH₂-OH | N | C(CH₃)₃ | H | 336.2 |
| 110 | H₃C-C(=O)-NH-CH₂CH₂CH₂CH₂-OH | N | C(CH₃)₃ | H | 364.2 |
| 111 | H₃C-C(=O)-NH-CH₂CH₂-N(CH₃)₂ | N | C(CH₃)₃ | H | 363.2 |
| 112 | H₃C-C(=O)-NH-CH₂CH₂-(pyrrolidin-1-yl) | N | C(CH₃)₃ | H | 389.2 |
| 113 | H₃C-C(=O)-NH-CH₂CH₂-(piperidin-1-yl) | N | C(CH₃)₃ | H | 403.2 |

TABLE 2-continued

| Ex. | R¹ | Y | Rᵃ | Rᵇ | M/s MH+ |
|---|---|---|---|---|---|
| 114 | acetamido-propyl-morpholine | N | tert-butyl | H | 419.2 |
| 115 | acetamido-ethyl-N,N-diethylamine | N | tert-butyl | H | 391.2 |
| 116 | acetamido-dihydrofuranone | N | tert-butyl | H | 376.1 |
| 117 | acetamido-ethyl-(1-methylpyrrolidin-2-yl) | N | tert-butyl | H | 403.2 |
| 118 | acetamido-ethoxy-ethanol | N | tert-butyl | H | 380.2 |
| 119 | acetamido-methyl-(1-methylpyrrol-2-yl) | N | tert-butyl | H | 385.2 |
| 120 | acetamido-ethoxy-ethyl | N | tert-butyl | H | 364.2 |
| 121 | acetamido-(S)-2-hydroxypropyl | N | tert-butyl | H | 350.2 |
| 122 | acetamido-(R)-2-hydroxypropyl | N | tert-butyl | H | 364.2 |
| 123 | acetamido-(S)-alanine ethyl ester | N | tert-butyl | H | 392.2 |
| 124 | acetamido-(2,2-diethoxyethyl) | N | tert-butyl | H | 408.2 |

TABLE 2-continued

| Ex. | R¹ | Y | Rᵃ | Rᵇ | M/s MH+ |
|---|---|---|---|---|---|
| 125 | acetamido-propyl isopropyl ether | N | tert-butyl | H | 392.2 |
| 126 | acetamido-propyl ethyl ether | N | tert-butyl | H | 378.2 |
| 127 | N-(2,3-dihydroxypropyl)acetamide | N | tert-butyl | H | 366.1 |
| 128 | 2-acetamido-2-methylpropanoic acid tert-butyl ester | N | tert-butyl | H | 434.2 |
| 129 | 1-acetyl-3-(methylsulfonyl)pyrrolidine | N | tert-butyl | H | 424.1 |
| 130 | N-(2-(pyridin-2-yl)ethyl)acetamide | N | tert-butyl | H | 397.2 |
| 131 | N-(1-hydroxy-2-methylpropan-2-yl)acetamide | N | tert-butyl | H | 364.2 |
| 132 | 3-acetamido-N-(2-oxotetrahydrofuran-3-yl)propanamide | N | tert-butyl | H | 447.2 |
| 133 | 1-acetylpyrrolidine-2-carboxamide | N | tert-butyl | H | 389.2 |
| 134 | 5-acetyl-4,5,6,7-tetrahydro-1H-imidazo[4,5-c]pyridine | N | tert-butyl | H | 398.2 |
| 135 | 1-acetyl-3-hydroxypyrrolidine | N | tert-butyl | H | 362.2 |

TABLE 2-continued

| Ex. | R¹ | Y | Rᵃ | Rᵇ | M/s MH+ |
|---|---|---|---|---|---|
| 136 | (S)-1-acetyl-3-hydroxypyrrolidine | N | tert-butyl | H | 362.2 |
| 137 | acetamido-pyrazole | N | tert-butyl | H | 358.2 |
| 138 | acetamido-ethyl-imidazole | N | tert-butyl | H | 386.2 |
| 139 | acetamido-ethyl-(1-isopropyl)imidazole | N | tert-butyl | H | 429.3 |
| 140 | acetamido-β-alanyl-neopentanol | N | tert-butyl | H | 449.17 |
| 141 | acetamido-(S)-propanediol | N | tert-butyl | H | 366.26 |
| 142 | acetamido-(R)-propanediol | N | tert-butyl | H | 366.3 |
| 143 | acetamido-methyl-(5-isopropyl)oxadiazole | N | tert-butyl | H | — |
| 144 | 2-methylpyrazine | N | tert-butyl | H | 327.2 |
| 145 | 2-bromo-5-methyl-thiadiazole | N | tert-butyl | H | 413.1 |
| 146 | 2,6-dimethylpyridine | N | tert-butyl | H | 340.2 |

Preparation of Certain Starting Materials

Abbreviations used are as follows: CDI is 1,1'-carbonyldiimidazole, DCM is dichloromethane, DIPEA is diisopropylethylamine, DMF is Dimethylformamide, THF is tetrahydrofuran, HPLC is High Performance Liquid Chromatography, DMF-DMA is N,N-Dimethylformamide dimethylacetal, DMSO is dimethyl sulfoxide, NMP is 1-Methyl-2-pyrrolidine, HCl is Hydrochloric acid, TFA is Trifluoroacetic acid, m-CPBA is meta-chloroperbenzoic acid.

(a) Aminothiazole Intermediates

The following aminothiazole intermediates of formula (A)

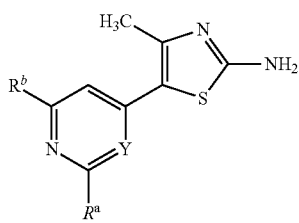

A are shown in Table 3 below, their method of preparation being described hereinafter.

TABLE 3

| Intermediate | Y | $R^a$ | $R^b$ | M/s MH+ |
|---|---|---|---|---|
| AA | C | —CH$_3$ | —CH$_3$ | 220.19 |
| AB | C | Cl | H | — |
| AC | N | —SCH$_3$ | —CH$_3$ | 253.02 |
| AD | N | —SOCH$_3$ | —CH$_3$ | — |
| AE | N | —SCH$_3$ | H | 239.03 |
| AF | N | —CH$_3$ | —CH$_3$ | 221.05 |
| AG | N | —C(CH$_3$)$_3$ | H | 249.12 |

Intermediate AA 5-(2,6-Dimethyl-pyridin-4-yl)-4-methyl-thiazol-2-ylamine

This is prepared as described in Example 20(b).

Intermediate AB 5-(2-Chloro-pyridin-4-yl)-4-methyl-thiazol-2-ylamine

AB1) 1-Bromo-1-(2-chloro-pyridin-4-yl)-propan-2-one

Bromine (1.36 ml, 26 mmol) is added dropwise to a stirred solution of 1-(2-chloro-pyridin-4-yl)-propan-2-one (Example 2a, 5.0 g, 29.5 mmol) in dioxane (150 ml) over 45 minutes at 5-10° C. After 20 minutes at room temperature the solvent is removed in vacuo to afford the titled compound as a yellow solid.

AB2) 5-(2-Chloro-pyridin-4-yl)-4-methyl-thiazol-2-ylamine

Thiourea (1.8 g, 29.4 mmol) is added to a stirred solution of 1-bromo-1-(2-chloro-pyridin-4-yl)-propan-2-one (7.3 g, 29.4 mmol) in ethanol (150 ml). The mixture is heated at 60° C. for 3 hours then allowed to cool to room temperature and stand for 18 h. The hydrobromide salt of the titled compound precipitates during this time and is removed by filtration and washed with diethyl ether.

Intermediate AC

4-Methyl-5-(6-methyl-2-methylsulfanyl-pyrimidin-4-yl)-thiazol-2-ylamine

AC1) 4,6-Dimethyl-2-methylsulfanyl-pyrimidine 4,6-Dimethyl-pyrimidine-2-thiol (20 g, 142 mmol) is added slowly to a solution of sodium hydroxide (6.3 g, 156 mmol) in ethanol (120 ml) and water (60 ml). Methyl iodide (9.8 ml, 156 mmol) is added dropwise and the mixture is stirred at room temperature for 1 hour. The solvents are removed in vacuo and the residue is partitioned between diethyl ether (200 ml) and water (200 ml). The organic extract is dried (MgSO$_4$) and the solvent is removed to give the titled compound.

AC2) 1-(6-Methyl-2-methylsulfanyl-pyrimidin-4-yl)-propan-2-one n-Butyllithium (1.6 M in hexanes, 67 ml, 107 mmol) is added dropwise to a stirred solution of diisopropylamine (15 ml, 107 mmol) in dry THF (90 ml) under argon at −78° C. After 15 minutes at −78° C. to 50° C. the mixture is cooled to −78° C. and a solution of 4,6-dimethyl-2-methylsulfanyl-pyrimidine (15 g, 97.4 mmol) in dry THF (45 ml) is added dropwise. The reaction is stirred for 2.5 hours at −78° C. then N-methoxy-N-methylacetamide (10.4 ml, 97.4 mmol) is added dropwise. The reaction is allowed to warm to room temperature over 1 hour followed by quenching with saturated aqueous ammonium chloride solution (10 ml). The mixture is concentrated to remove most of the THF then partitioned between water (200 ml) and DCM (200 ml). The organic extract is separated, dried (MgSO$_4$), and the solvent is removed to afford the titled compound. The material is a mixture of keto and enol forms as observed by $^1$H nmr (CDCl$_3$)

AC3) 1-Bromo-1-(6-methyl-2-methylsulfanyl-pyrimidin-4-yl)-propan-2-one

Bromine (1.46 ml, 28.5 mmol) is added to a rapidly stirred cooled (5-10° C.) solution of 1-(6-methyl-2-methylsulfanyl-pyrimidin-4-yl)-propan-2-one (7.0 g, 35 mmol) in dioxane (100 ml) over 30 minutes. The reaction is allowed to warm to room temperature and the solvent is removed in vacuo to yield the titled compound which is used immediately in the next step.

AC4) 4-Methyl-5-(6-methyl-2-methylsulfanyl-pyrimidin-4-yl)-thiazol-2-ylamine

Thiourea (2.7 g, 35 mmol) is added to a stirred solution of 1-bromo-1-(6-methyl-2-methylsulfanyl-pyrimidin-4-yl)-propan-2-one (AC3) in ethanol (100 ml) at 60° C. After 30 minutes the reaction is allowed to cool to room temperature. After standing for 18 hours the hydrobromide salt of the titled compound is removed by filtration and washed with diethyl ether. The product is dissolved in water and 2M sodium hydroxide is added to precipitate the titled compound as the free base.

Intermediate AD

5-(2-Methanesulfinyl-6-methyl-pyrimidin-4-yl)-4-methyl-thiazol-2-ylamine m-CPBA (57-86% purity, 6.0 g, 20-30 mmol) is added in portions to a rapidly stirring solution/suspension of 4-methyl-5-(6-methyl-2-methylsulfanyl-pyrimidin-4-yl)-thiazol-2-ylamine (6.0 g, 23.8 mmol) in dry dichloromethane (200 ml) at 0° C. After the addition (15 minutes) the reaction is allowed to warm slowly to room temperature. The mixture is cautiously added to saturated sodium bicarbonate solution (300 ml), shaken, and the organic extract is separated and dried (MgSO$_4$). This first extract contains a 1:1 mixture of sulfoxide and sulfone. The aqueous phase is then partitioned with chloroform to extract the titled compound as yellow solid.

Intermediate AE

4-Methyl-5-(2-methylsulfanyl-pyrimidin-4-yl)-thiazol-2-ylamine

This material is prepared by the procedure outlined for intermediate AC, replacing 4,6-dimethyl-pyrimidine-2-thiol in the first step (AC1) with 4-methyl-2-methylsulfanyl-pyrimidine.

Intermediate AF

5-(2,6-Dimethyl-pyrimidin-4-yl)-4-methyl-thiazol-2-ylamine

AF1) 2,4,6-Trimethyl-pyrimidine

This material is prepared following the protocols described in *Helvetica Chimica Acta*, Vol. 64, No. 1, pp 113-152, 1981. (Authors: K. Burdeska, H. Fuhrer, G. Kabas and A. E. Siegrist)

AF2) 1-Bromo-1-(2,6-dimethyl-pyrimidin-4-yl)-propan-2-one

This material is prepared from 2,4,6-trimethyl-pyrimidine following the 2-step protocol used to prepare 1-bromo-1-(6-methyl-2-methylsulfanyl-pyrimidin-4-yl)-propan-2-one (AC3) from 4,6-dimethyl-2-methylsulfanyl-pyrimidine (AC1).

AF3) 5-(2,6-Dimethyl-pyrimidin-4-yl)-4-methyl-thiazol-2-ylamine

This material is prepared by reaction of 1-bromo-1-(2,6-dimethyl-pyrimidin-4-yl)-propan-2-one with thiourea following the procedure described for intermediate AC4.

Intermediate AG

5-(2-tert-Butyl-pyrimidin-4-yl)-4-methyl-thiazol-2-ylamine

This compound is prepared by two different methods:
Method a:
The titled compound is prepared by an analogous procedure to N-[4-Methyl-5-(2-morpholin-4-yl-pyrimidin-4-yl)-thiazol-2-yl]-acetamide (25e) by replacing morpholinoformamidine hydrobromide (part 25c) with tert-butylcarbamide hydrochloride.

Method b:

AG1) 2-tert-Butyl-4-methyl-pyrimidine

Following a protocol described in *Helvetica Chimica Acta*, Vol. 64, No. 1, pp 113-152, 1981. (Authors: K. Burdeska, H. Fuhrer, G. Kabas and A. E. Siegrist), sodium methoxide (30% wt in methanol, 28 ml, 146 mmol) is added dropwise over 2 hours to a stirred solution of tert-butylcarbamide hydrochloride (10 g, 73 mmol) and acetylacetaldehyde dimethyl acetal (10.75 ml, 80 mmol) in methanol at 60° C. After stirring for an additional 6 hours at 50° C. the solvent is removed in vacuo and the residue is diluted with water (500 ml). The solution is brought to pH 7.0 by addition of 6M HCl and extracted with dichloromethane (3×300 ml). After drying (MgSO$_4$) the solvent is removed to give the product as an oil.

AG2) 1-(2-tert-Butyl-pyrimidin-4-yl)-propan-2-one

This material is prepared from 2-tert-butyl-4-methyl-pyrimidine following the protocol outlined for intermediate AC2.

AG3) 1-Bromo-1-(2-tert-butyl-pyrimidin-4-yl)-propan-2-one

Bromine (3.25 g, 20.7 mmol) in chloroform (20 ml) is added dropwise over 5 hours to a stirred solution of 1-(2-tert-butyl-pyrimidin-4-yl)-propan-2-one (4.0 g, 20.7 mmol) in dioxane (300 ml) maintained at 10-15° C. When the addition is complete the solvent is removed in vacuo to give the titled compound as a hydrobromide salt.

AG4) 5-(2-tert-Butyl-pyrimidin-4-yl)-4-methyl-thiazol-2-ylamine

1-Bromo-1-(2-tert-butyl-pyrimidin-4-yl)-propan-2-one (1 g, 37 mmol) is stirred in ethanol (40 ml) at 70° C. Thiourea (280 mg, 37 mmol) is added and stirring continued for 1 hour at 70° C. After cooling to room temperature the mixture is filtered to afford the titled compound as the hydrobromide salt. If required, the product is dissolved in 1M aqueous hydrochloric acid and the solution is brought to pH 8 by addition of sodium hydroxide solution to precipitate the titled compound as the free base.

(b) Imidazole-Urea Intermediates

The following imidazole-urea intermediates of formula (B)

B are shown in Table 4 below, the method of preparation being described hereinafter.

TABLE 4

| Intermediate | Y | R$^a$ | R$^b$ | Starting material | Method |
|---|---|---|---|---|---|
| BA | C | —CH$_3$ | —CH$_3$ | AA | Ba |
| BB | C | Cl | H | AB | Bb |
| BC | N | —SCH$_3$ | —CH$_3$ | AC | Bb |
| BD | N | —SOCH$_3$ | —CH$_3$ | AD | Bb |
| BE | N | —SCH$_3$ | H | AE | Bb |
| BF | N | —CH$_3$ | —CH$_3$ | AF | Ba |
| BG | N | —C(CH$_3$)$_3$ | H | AG | Ba |

Method (Ba)

A suspension of the aminothiazole (13.4 mmol) and 1,1'-carbonyldiimidazole (2.4 g, 14.7 mmol, 1.1 equivalents) in CH$_2$Cl$_2$ (75 ml) is heated at 40° C.—reflux under argon until no starting material remains (30 minutes to 5 hours) as determined by HPLC and NMR. When cool the solid precipitate is removed by filtration. This solid consists of the imidazole-urea intermediate (B) together with variable amounts of the corresponding isocyanate and imidazole. This solid is used in the subsequent steps since the imidazole-urea intermediate and isocyanate intermediate are equally suitable as precursors to ureas.

The following intermediates are prepared by this method: imidazole-1-carboxylic acid [5-(2,6-dimethyl-pyridin-4-yl)-4-methyl-thiazol-2-yl]-amide (BA), Imidazole-1-carboxylic acid [5-(2-tert-butyl-pyrimidin-4-yl)-4-methyl-thiazol-2-yl]-amide (BG), Imidazole-1-carboxylic acid [5-(2,6-dimethyl-pyrimidin-4-yl)-4-methyl-thiazol-2-yl]-amide (BF).

Method (Bb)

Triethylamine or sodium hydride (7.17 mmol, 1.1 equivalents) is added to a stirred suspension of the aminothiazole (free base or hydrobromide salt, 6.53 mmol) and carbonyldiimidazole (1-2 equivalents) in dry CH$_2$Cl$_2$ (40 ml) containing a few drops of DMF to aid solubility if necessary. The reaction is heated at reflux under argon until no starting material remains (18 hours) as determined by HPLC and NMR. When cool the solid precipitate is removed by filtration and washed with diethyl ether. This solid consists of the imidazole-urea intermediate (B) together with variable amounts of the corresponding isocyanate and imidazole. This solid is used in the subsequent steps since the imidazole-urea intermediate and isocyanate intermediate are equally suitable as precursors to ureas.

The following intermediates are prepared by this method: imidazole-1-carboxylic acid [5-(2-chloro-pyridin-4-yl)-4-methyl-thiazol-2-yl]-amide (BB), imidazole-1-carboxylic acid [4-methyl-5-(6-methyl-2-methylsulfanyl-pyrimidin-4-yl)-thiazol-2-yl]-amide (BC), imidazole-1-carboxylic acid [5-(2-methanesulfinyl-6-methyl-pyrimidin-4-yl)-4-methyl-thiazol-2-yl]-amide (BD), and imidazole-1-carboxylic acid [5-(2-methanesulfinyl-pyrimidin-4-yl)-4-methyl-thiazol-2-yl]-amide (BE).

(c) Amine Intermediates

Many of the amine intermediates (C) that are used to prepare the final compounds of Examples in Table 2 are commercially available or are prepared by standard methods. The preparation of certain amine intermediates that are not readily commercially available is given below. Those are the following amine intermediates of formula (C)

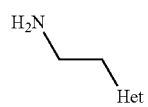

where Het is one of the following:

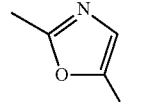

CA

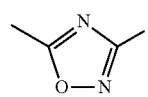

CB

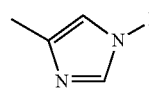

CC

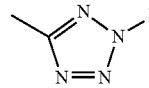

CD

and are as shown in Table 5 below.

TABLE 5

| Intermediate | Het | R |
|---|---|---|
| CA | CA | —CH$_2$CH$_3$ |
| CB | CB | —CH$_2$CH$_3$ |
| CC1 | CC | —CH$_2$CH$_3$ |
| CC2 | CC | —CH$_2$CH$_2$CH$_3$ |
| CC3 | CC | —CH(CH$_3$)$_2$ |
| CD | CD | —CH$_2$CH$_3$ |

Intermediate CA 2-(5-Ethyl-oxazol-2-yl)-ethylamine (Prepared previously)

Step 1) [2-(2-Hydroxy-butylcarbamoyl)-ethyl]-carbamic acid benzyl ester

A mixture comprising Z-Beta-Ala-OH (9.0 g, 40.3 mmol), EDCI.HCl (10.0 g, 52.4 mmol), hyrdoxybenzotriazole (5.45 g, 40.3 mmol), triethylamine (7.3 ml, 52.4 mmol) in DCM (150 ml) is stirred at 0° C. for 30 minutes. 1-Amino-2-butanol (4.2 ml, 44.3 mmol) is added in one portion and stirring is continued for 1 hour. The reaction mixture is diluted with water (150 ml) and extracted with dichloromethane (2×150 ml) The organic layers are combined, dried over MgSO$_4$, filtered and concentrated in vacuo to yield a crude white solid. The product is purified by chromatography on silica eluting with ethanol-ethyl acetate (1:10) to give the titled compound.

Step 2) [2-(2-Oxo-butylcarbamoyl)-ethyl]-carbamic acid benzyl ester

To a stirred solution of oxalyl chloride (2 M in DCM) (13.35 ml, 26.5 mmol) in dry DCM at −78° C. is added dropwise DMSO (2.5 ml, 35.4 mmol). After stirring for 15 minutes, the reaction mixture is treated with a solution of [2-(2-hydroxy-butylcarbamoyl)-ethyl]-carbamic acid benzyl ester (step 1) (6.5 g, 22.1 mol) in dry DCM (40 ml). Triethylamine (13 ml) is added after 1 hour and after stirring at −78° C. for 90 minutes, the reaction mixture is allowed to warm to room temperature. The reaction is diluted with DCM (100 ml) and washed with HCl (1M, 200 ml), saturated sodium bicarbonate solution (200 ml), water (200 ml) and brine (200 ml). The organic portion is dried over $MgSO_4$, filtered and concentrated in vacuo to yield the titled compound as a white solid.

Step 3) [2-(5-Ethyl-oxazol-2-yl)-ethyl]-carbamic acid benzyl ester

To a stirred suspension of polymer supported triphenylphosphene (19.6 g, 58.9 mmol) in DCM (250 ml) is added iodine (14.95 g, 58.9 mmol). After stirring at room temperature for 10 minutes, the mixture is treated with triethylamine (16.4 ml, 117.5 mmol) followed by a solution of [2-(2-oxo-butylcarbamoyl)-ethyl]-carbamic acid benzyl ester (step 2) (6.88 g, 23.5 mmol) in DCM (50 ml). The reaction mixture is stirred overnight and then filtered through Celite™ filter material, washed through with DCM (500 ml) and the solvent removed in vacuo to yield the titled compound as a brown solid.

Step 4) 2-(5-Ethyl-oxazol-2-yl)-ethylamine

Ammonium formate (0.316 g, 5 mmol) is added to a solution of [2-(5-ethyl-oxazol-2-yl)-ethyl]-carbamic acid benzyl ester (step 3) (1.66 mmol) in methanol (15 ml) and 10% Pd on carbon (125 mg) is added under an inert atmosphere. The mixture is stirred at ambient temperature for 2 hours. The catalyst is removed by filtration and the filtrate is evaporated. The residue is diluted with dichloromethane, filtered to remove undissolved solid and the solvent is removed. The residue is dissolved in DCM and treated with 1M aqueous sodium hydroxide solution (5 ml). The organic extract is separated, dried ($MgSO_4$), filtered and the solvent is removed. Crystallisation from ethyl acetate/dichloromethane affords the titled compound.

Intermediate CB 2-(3-Ethyl-[1,2,4]oxadiazol-5-yl)-ethylamine

Step 1) N-Hydroxy-propionamidine

Ethanol (100 ml) followed by hydroxylamine hydrochloride (5.0 g, 72 mmol) is added to a solution of $K_2CO_3$ (9.93 g, 72 mmol) in water (25 ml). Propionitrile (5.13 ml, 72 mmol) is then added and the mixture is heated at reflux for 18 hours. After cooling, the solvent is removed in vacuo and ethanol is added to dissolve the product. The solution is separated from any undissolved solid and the solvent is removed to leave the titled compound as a yellow oil.

Step 2) [2-(3-Ethyl-[1,2,4]oxadiazol-5-yl)-ethyl]-carbamic acid tert-butyl ester N-Hydroxy-propionamidine (0.10 g, 1.15 mmol) in DMF (2 ml) is added to a stirred suspension of sodium hydride (0.05 g of a 60% dispersion in oil, 1.26 mmol) in DMF (20 ml) in the presence of molecular sieves (0.1 g). The reaction flask is then immersed in a pre-heated oil bath at 50° C. and stirring continued for 5 min. 3-tert-Butoxycarbonylamino-propionic acid ethyl ester (0.25 g, 1.15 mmol) in DMF (2 ml) is added over 5 minutes. After 3 hours at 50° C. the mixture is cooled to 0° C. and water (3 ml) is added. The mixture is allowed to warm to room temperature then filtered through Celite™ filter material, washing with ethyl acetate, and the solvent is removed. Purification by chromatography, eluting with hexane:ethyl acetate (3:1) affords the titled compound.

Step 3) 2-(3-Ethyl-[1,2,4]oxadiazol-5-yl)-ethylamine

TFA (0.5 ml) is added to a stirred solution of [2-(3-propyl-[1,2,4]oxadiazol-5-yl)-ethyl]-carbamic acid tert-butyl ester (0.093 g, 0.39 mmol) in DCM (1 ml). After 1 hour the solvents are removed to afford the titled compound.

Intermediates CC1, CC2, CC3

These compounds, namely 2-(1-ethyl-1H-imidazol-4-yl)-ethylamine (CC1), 2-(1-propyl-1H-imidazol-4-yl)-ethylamine (CC2) and 2-(1-isopropyl-1H-imidazol-4-yl)-ethylamine (CC3) are prepared by alkylation of 7,8-dihydro-6H-imidazo[1,5-c]pyrimidin-5-one with the appropriate alkyl bromide followed by hydrolysis as described in R. Jain and L. A. Cohen, *Tetrahedron*, (1996), 52, 5363-5370.

Intermediate CD 2-(2-Ethyl-1H-tetrazol-5-yl)-ethylamine

Step 1) [2-(2-Ethyl-2H-tetrazol-5-yl)-ethyl]-carbamic acid tert-butyl ester

A solution of [2-(1H-tetrazol-5-yl)-ethyl]-carbamic acid tert-butyl ester (prepared by the protocols outlined in N. A. Delaney, G. C. Rovnyak and M. Loots, European Patent specification EP 449523) (1.0 g, 4.69 mmol) in dry THF (20 ml) is treated with a 60% dispersion of sodium hydride in mineral oil (0.19 g, 4.69 mmol) and stirred at ambient temperature for 10 minutes. Ethyliodide (0.375 ml, 4.69 mmol) is added and the reaction mixture is heated at reflux for 7 hours, then diluted with ethyl acetate and filtered. The filtrate is evaporated and the residue purified by flash silica chromatography (elution 3:2 hexane/ethyl acetate) to afford the titled compound, [2-(2-ethyl-2H-tetrazol-5-yl)-ethyl]-carbamic acid tert-butyl ester, eluted first and [2-(1-ethyl-1H-tetrazol-5-yl)-ethyl]-carbamic acid tert-butyl ester, eluted second.

Step 2) 2-(2-Ethyl-1H-tetrazol-5-yl)-ethylamine

[2-(2-Ethyl-2H-tetrazol-5-yl)-ethyl]-carbamic acid tert-butyl ester (0.33 g, 1.36 mmol) is dissolved in dichloromethane (3 ml) and treated with trifluoroacetic acid (1 ml) and stirred at ambient temperature for 3 hours. The solvent is removed to afford the titled compound as the TFA salt.
(d) Thiourea Intermediates
The following thiourea intermediates of formula (D)

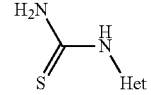

where Het is one of the following:

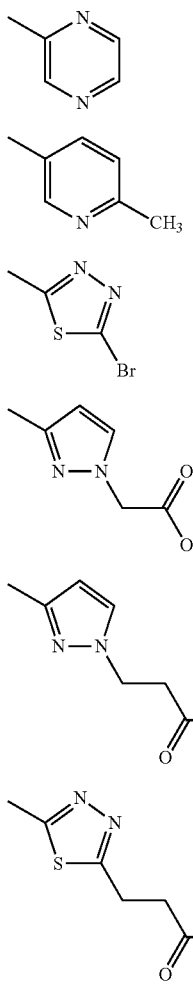

are prepared as described hereinafter.

Intermediate DA

Pyrazin-2-yl-thiourea

The preparation of this material is described previously (Example 1a)

Intermediates DB and DC

Namely, (6-Methyl-pyridin-3-yl)-thiourea (DB) and (5-Bromo-[1,3,4]thiadiazol-2-yl)-thiourea (DC), are prepared by a similar process to pyrazin-2-yl-thiourea (DA) by replacing aminopyrazine in Example 1a with the appropriate heterocyclic amine Intermediate DD (3-Thioureido-pyrazol-1-yl)-acetic acid Step 1) 2-(1H-Pyrazol-3-yl)-isoindole-1,3-dione 1H-Pyrazol-3-ylamine (2 g, 24 mmol) and 1,3-dioxo-1,3-dihydro-isoindole-2-carboxylic acid ethyl ester (5.3 g, 24 mmol) are stirred in THF (70 ml) at room temperature for 18 hours. The reaction mixture is then concentrated to half volume and filtered to remove the titled compound which is washed with methanol followed by diethyl ether.

Step 2) [3-(1,3-Dioxo-1,3-dihydro-isoindol-2-yl)-pyrazol-1-yl]-acetic acid tert-butyl ester Sodium hydride (60% in oil, 0.538 g, 13.4 mmol) is added to a stirred solution of 2-(1H-pyrazol-3-yl)-isoindole-1,3-dione (2.39 g, 11.2 mmol) in dry DMF (25 ml) at room temperature. After 10 minutes tert-butyl bromoacetate (1.81 ml, 11.2 mmol) is added and the reaction is stirred for 18 hours. The reaction is quenched with water (1 ml), ethyl acetate (150 ml) is added and the organic phase is washed with water (3×100 ml) followed by brine (1×100 ml). The solvent is removed and the product is purified by chromatography on silica (gradient elution: ethyl acetate—hexane) to give the titled compound.

Step 3) (3-Amino-pyrazol-1-yl)-acetic acid tert-butyl ester

Hydrazine hydrate (0.27 ml, 6.69 mmol) is added to a stirred solution of [3-(1,3-dioxo-1,3-dihydro-isoindol-2-yl)-pyrazol-1-yl]-acetic acid tert-butyl ester (2.18 g, 6.69 mmol) in ethanol (12 ml). The reaction is stirred at 90° C. for 2.5 hours. When cool, the reaction is diluted with ethanol (50 ml) and the white precipitate is removed by filtration, washing with more ethanol (250 ml). The combined filtrate is evaporated to dryness and dichloromethane (100 ml) is added. After filtering again, the filtrate is evaporated to give the titled compound as a colourless oil.

Step 4) [3-(3-Benzoyl-thioureido)-pyrazol-1-yl]-acetic acid tert-butyl ester (3-Amino-pyrazol-1-yl)-acetic acid tert-butyl ester (1.05 g, 5.33 mmol) is added dropwise under argon to a stirred solution of benzoyl isothiocyanate (0.754 ml, 5.4 mmol). After stirring for 5 minutes the reaction mixture is poured onto water and the titled compound, a yellow precipitate, is collected and dried.

Step 5) (3-Thioureido-pyrazol-1-yl)-acetic acid

A stirred suspension of [3-(3-benzoyl-thioureido)-pyrazol-1-yl]-acetic acid tert-butyl ester (0.823 g, 2.28 mmol) in 2M NaOH (2 ml) is heated at 100° C. for 30 minutes. When cool, the mixture is acidified to pH 3 with 1M HCl. The mixture is extracted with ethyl acetate. The organic phase is separated and the aqueous phase is evaporated to dryness to afford the titled compound as a hydrochloride salt mixed with sodium chloride.

Intermediate DE 3-(3-Thioureido-pyrazol-1-yl)-propionic acid

This material is prepared by an analogous procedure to (3-thioureido-pyrazol-1-yl)-acetic acid (intermediate DD) by replacing tert-butyl bromoacetate in step 2 with 3-bromo-propionic acid tert-butyl ester.

Intermediate DF

3-(5-Thioureido-[1,3,4]thiadiazol-2-yl)-propionic acid

Step 1) 3-(5-Amino-[1,3,4]thiadiazol-2-yl)-propionic acid methyl ester

3-Chlorocarbonyl-propionic acid methyl ester (4.4 g, 29 mmol) is added dropwise to a stirred suspension of semicarbazide (4.0 g, 44 mmol) in THF (25 ml) at 0° C. After stirring at room temperature for 1 hour, the solvent is removed to give a white solid. Toluene (30 ml) is added followed by dropwise addition of methane sulfonic acid (3.37 ml, 52 mmol) then the reaction is heated at 70° C. for 3 hours. The mixture is concentrated in vacuo and methanol (30 ml) is added. Aqueous ammonia is then added with stirring until a basic mixture is obtained. The solvents are removed and the residue is purified by chromatography on silica eluting with chloroform:methanol (10:1) to give the titled product.

Step 2) Carbethoxy-3-(5-thioureido-[1,3,4]thiadiazol-2-yl)-propionic acid methyl ester Carbethoxyisocyanate (0.49 ml, 3.73 mmol) in dry dichloromethane (10 ml) is added dropwise at room temperature to a stirred suspension of 3-(5-amino-[1,3,4]thiadiazol-2-yl)-propionic acid methyl ester (0.666 g, 3.56 mmol) in DCM (20 ml). The reaction is stirred under argon at room temperature for 18 h then the solvent is removed to afford the titled compound.

Step 3) 3-(5-Thioureido-[1,3,4]thiadiazol-2-yl)-propionic acid

Carbethoxy-3-(5-thioureido-[1,3,4]thiadiazol-2-yl)-propionic acid methyl ester (0.675 g, 2.91 mmol) is suspended in 2M NaOH (8 ml) and the reaction is stirred at reflux for 3.5 hours. When cool, the solution is acidified to pH 3 with 6M HCl and the titled compound is removed by filtration and dried.

Preparation of Specific Examples

General Procedure A for Preparing Ureas by Reacting Imidazole-Urea Intermediates of Formula B with Amine Intermediates of Formula C The amine (0.12 mmol) is added to a solution/suspension of the imidazole urea intermediate (0.11 mmol) in DMF (1.0 ml). Triethylamine may be added to enhance reaction rate and especially if one or both of the starting materials is present as a salt (1.1 equivalents Et₃N per equiv. salt). The reaction mixture is sonicated if necessary until a clear solution is obtained. The reaction is allowed to proceed at between room temperature and 70° C. until the starting material is consumed (30 min to 24 hours). When complete, the mixture is concentrated in vacuo to remove the solvent. The product is conveniently purified by dissolving the crude residue in THF (2 ml) and adding this to polymer supported isocyanate (Argonaut Technologies, 0.5 g, 1.10 mmol) which has been pre-swollen with THF (2 ml). The reaction mixture is allowed to drip through the resin under gravity and the solvent is removed in vacuo to yield the titled compound. Alternatively the product is purified by a standard procedure e.g. crystallisation, chromatography or HPLC.

Example 31

3-{3-[5-(2,6-Dimethyl-pyridin-4-yl)-4-methyl-thiazol-2-yl]-ureido}-N,N-dimethyl-propionamide To a stirred solution of imidazole-1-carboxylic acid [5-(2,6-dimethyl-pyridin-4-yl)-4-methyl-thiazol-2-yl]-amide (Intermediate BA) (0.05 g, 0.16 mmol) in DMF (1.5 ml) under an inert atmosphere is added 3-amino-N,N-dimethyl-propionamide (Amine) (0.018 g, 0.16 mmol). The reaction mixture is stirred at room temperature for 18 hours. The solvent is removed in vacuo and the resulting crude residue is dissolved in THF and passed through a plug of polymer supported isocyanate resin (0.5 g, pre-washed with THF). The solution is concentrated in vacuo and the crude residue is trituated with ether-ethyl acetate to afford the titled compound as a yellow solid.

Examples 32-38

These compounds, namely 2-{3-[5-(2,6-dimethyl-pyridin-4-yl)-4-methyl-thiazol-2-yl]-ureido}-N,N-dimethyl-acetamide, 1-[5-(2-chloro-pyridin-4-yl)-4-methyl-thiazol-2-yl]-3-[2-(5-ethyl-oxazol-2-yl)-ethyl]-urea, 1-[5-(2-chloro-pyridin-4-yl)-4-methyl-thiazol-2-yl]-3-[2-(1-ethyl-1H-imidazol-4-yl)-ethyl]-urea, 1-[5-(2-chloro-pyridin-4-yl)-4-methyl-thiazol-2-yl]-3-[2-(1-propyl-1H-imidazol-4-yl)-ethyl]-urea, 1-[5-(2-chloro-pyridin-4-yl)-4-methyl-thiazol-2-yl]-3-[2-(1-isopropyl-1H-imidazol-4-yl)-ethyl]-urea, 1-[5-(2-chloro-pyridin-4-yl)-4-methyl-thiazol-2-yl]-3-[2-(2-ethyl-2H-tetrazol-5-yl)-ethyl]-urea and 1-[2-(5-ethyl-oxazol-2-yl)-ethyl]-3-[4-methyl-5-(6-methyl-2-methylsulfanyl-pyrimidin-4-yl)-thiazol-2-yl]-urea are prepared by general procedure A using the appropriate imidazole urea intermediate (B) and amine (C).

Example 39

N-(5-{2-[(2-Dimethylamino-ethyl)-methyl-amino]-6-methyl-pyrimidin-4-yl}-4-methyl-thiazol-2-yl)-acetamide

Step 1) N-[4-(2-Amino-4-methyl-thiazol-5-yl)-6-methyl-pyrimidin-2-yl]-N,N',N'-trimethyl-ethane-1,2-diamine N,N,N'-Trimethyl-ethane-1,2-diamine (0.62 g, 6.16 mmol) is added to a stirred solution of 5-(2-methanesulfinyl-6-methyl-pyrimidin-4-yl)-4-methyl-thiazol-2-ylamine (Intermediate AD, 0.33 g, 1.23 mmol) in NMP (15 ml). The reaction is heated at 70° C. for 18 hours then the solvent is removed in vacuo. The residue is purified by reverse phase chromatography (C18 Jones Flashmaster™ chromatographic system, gradient elution conditions MeCN/H₂O) to give the titled product.

Step 2) N-(5-{2-[(2-Dimethylamino-ethyl)-methylamino]-6-methyl-pyrimidin-4-yl}-4-methyl-thiazol-2-yl)-acetamide N-[4-(2-Amino-4-methyl-thiazol-5-yl)-6-methyl-pyrimidin-2-yl]-N,N',N'-trimethyl-ethane-1,2-diamine (0.020 g, 0.065 mmol) in acetic anhydride (1 ml) is heated at 60° C. for 2 hours. When cool, the solvent is removed in vacuo and the residue is partitioned between ethyl acetate (30 ml) and water (30 ml). The organic extract is removed, dried (MgSO$_4$) and the solvent removed to give the titled compound.

Example 40

1-[2-(5-Ethyl-oxazol-2-yl)-ethyl]-3-[5-(2-methane-sulfinyl-6-methyl-pyrimidin-4-yl)-4-methyl-thiazol-2-yl]-urea This compound is prepared by oxidation of 1-[2-(5-ethyl-oxazol-2-yl)-ethyl]-3-[4-methyl-5-(6-methyl-2-methylsulfanyl-pyrimidin-4-yl)-thiazol-2-yl]-urea with m-CPBA (meta-chloroperoxy-benzoic acid) following the protocol used to prepare 5-(2-Methanesulfinyl-6-methyl-pyrimidin-4-yl)-4-methyl-thiazol-2-ylamine (intermediate AD).

Example 41

1-[2-(5-Ethyl-oxazol-2-yl)-ethyl]-3-[5-(2-methane-sulfonyl-6-methyl-pyrimidin-4-yl)-4-methyl-thiazol-2-yl]-urea Meta-chloroperoxybenzoic acid or m-CPBA (57-86% purity, 0.438 g, 1.8 mmol) is added in portions to a rapidly stirring solution of 1-[2-(5-ethyl-oxazol-2-yl)-ethyl]-3-[5-(2-methane-sulfinyl-6-methyl-pyrimidin-4-yl)-4-methyl-thiazol-2-yl]-urea (0.31 g, 0.74 mmol) in dry dichloromethane (5 ml) at room temperature. After 2 hours the mixture is diluted with dichloromethane and washed with aqueous sodium thiosulfite and brine. The organic extract is separated, dried over MgSO$_4$ and the solvent is removed. Purification by chromatography on silica, eluting with EtOAc, MeOH (97:3) affords the titled compound.

Example 42

1-[5-(2-Dimethylamino-6-methyl-pyrimidin-4-yl)-4-methyl-thiazol-2-yl]-3-[2-(5-ethyl-oxazol-2-yl)-ethyl]-urea A solution of 1-[2-(5-ethyl-oxazol-2-yl)-ethyl]-3-[5-(2-methanesulfonyl-6-methyl-pyrimidin-4-yl)-4-methyl-thiazol-2-yl]-urea (0.22 g, 0.049 mmol) and dimethylamine (2M in THF, 0.073 ml, 0.15 mmol) in DMF (1 ml) is heated at 70° C. for 18 hours. The solvent is removed and the product is purified by chromatography on silica eluting with ethyl acetate to give the titled compound.

Example 43

1-(5-{2-[(2-Dimethylamino-ethyl)-methyl-amino]-6-methyl-pyrimidin-4-yl}-4-methyl-thiazol-2-yl)-3-[2-(5-ethyl-oxazol-2-yl)-ethyl]-urea A solution of 1-[2-(5-Ethyl-oxazol-2-yl)-ethyl]-3-[5-(2-methanesulfinyl-6-methyl-pyrimidin-4-yl)-4-methyl-thiazol-2-yl]-urea (Example 40) (0.25 g, 0.58 mmol) and N,N,N-trimethyl-ethylenediamine (0.368 ml, 2.9 mmol) in DMF (3 ml) is heated at 90° C. for 2 hours until no starting material remains. The solvent is removed and the residue is purified by chromatography (silica, ethyl acetate-methanol gradient elution) to afford the titled compound.

Example 44-54

These compounds, namely 1-[2-(5-ethyl-oxazol-2-yl)-ethyl]-3-[5-(2-imidazol-1-yl-6-methyl-pyrimidin-4-yl)-4-methyl-thiazol-2-yl]-urea, 1-[2-(5-ethyl-oxazol-2-yl)-ethyl]-3-{4-methyl-5-[6-methyl-2-(2-morpholin-4-yl-ethylamino)-pyrimidin-4-yl]-thiazol-2-yl}-urea, 1-(5-{2-[(2-dimethylamino-ethyl)-ethyl-amino]-6-methyl-pyrimidin-4-yl}-4-methyl-thiazol-2-yl)-3-[2-(5-ethyl-oxazol-2-yl)-ethyl]-urea, 1-(5-{2-[(2-diethylamino-ethyl)-methyl-amino]-6-methyl-pyrimidin-4-yl}-4-methyl-thiazol-2-yl)-3-[2-(5-ethyl-oxazol-2-yl)-ethyl]-urea, 1-{5-[2-(3-dimethylamino-propylamino)-6-methyl-pyrimidin-4-yl]-4-methyl-thiazol-2-yl}-3-[2-(5-ethyl-oxazol-2-yl)-ethyl]-urea, 1-[2-(5-ethyl-oxazol-2-yl)-ethyl]-3-{5[2-(3-imidazol-1-yl-propyl-amino)-6-methyl-pyrimidin-4-yl]-4-methyl-thiazol-2-yl}-urea, 1-(5-{2-[(3-dimethylamino-propyl)-methyl-amino]-6-methyl-pyrimidin-4-yl}-4-methyl-thiazol-2-yl)-3-[2-(5-ethyl-oxazol-2-yl)-ethyl]-urea, 1-{5-[2-(2-diethylamino-ethylamino)-6-methyl-pyrimidin-4-yl]-4-methyl-thiazol-2-yl}-3-[2-(5-ethyl-oxazol-2-yl)-ethyl]-urea, 1-(5-{2-[(3-amino-propyl)-methyl-amino]-6-methyl-pyrimidin-4-yl}-4-methyl-thiazol-2-yl)-3-[2-(5-ethyl-oxazol-2-yl)-ethyl]-urea, 1-[2-(5-ethyl-oxazol-2-yl)-ethyl]-3-(4-methyl-5-{6-methyl-2-[3-(4-methyl-piperazin-1-yl)-propylamino]-pyrimidin-4-yl}-thiazol-2-yl)-urea, 1-[2-(5-ethyl-oxazol-2-yl)-ethyl]-3-(4-methyl-5-{6-methyl-2-[methyl-(2-morpholin-4-yl-ethyl)-amino]-pyrimidin-4-yl}-thiazol-2-yl)-urea are prepared from 1-[2-(5-ethyl-oxazol-2-yl)-ethyl]-3-[5-(2-methanesulfinyl-6-methyl-pyrimidin-4-yl)-4-methyl-thiazol-2-yl]-urea (Example 40) by an analogous procedure to Example 43 using the appropriate amine.

Example 55

1-[2-(5-Ethyl-oxazol-2-yl)-ethyl]-3-(4-methyl-5-{6-methyl-2-[(pyrrolidin-2-ylmethyl)-amino]-pyrimidin-4-yl}-thiazol-2-yl)-urea Step 1) 2-{[4-(2-{3-[2-(5-Ethyl-oxazol-2-yl)-ethyl]-ureido}-4-methyl-thiazol-5-yl)-6-methyl-pyrimidin-2-ylamino]-methyl}-pyrrolidine-1-carboxylic acid tert-butyl ester This material is prepared from 1-[2-(5-ethyl-oxazol-2-yl)-ethyl]-3-[5-(2-methanesulfinyl-6-methyl-pyrimidin-4-yl)-4-methyl-thiazol-2-yl]-urea (Example 40) and 2-aminomethyl-pyrrolidine-1-carboxylic acid tert-butyl ester by an analogous procedure to Example 42 but replacing DMF by dioxane.

Step 2) 1-[2-(5-Ethyl-oxazol-2-yl)-ethyl]-3-(4-methyl-5-{6-methyl-2-[(pyrrolidin-2-ylmethyl)-amino]-pyrimidin-4-yl}-thiazol-2-yl)-urea 2-Aminomethyl-pyrrolidine-1-carboxylic acid tert-butyl ester (0.299 mmol) is dissolved in TFA (2.5 ml) at room temperature. After 18 hours, the mixture is diluted with aqueous NaOH and the product is extracted into ethyl acetate. The organic extract is separated, dried over MgSO$_4$ and the solvent is removed to give the titled compound.

Example 56

1-[2-(5-Ethyl-oxazol-2-yl)-ethyl]-3-[5-(2-methoxy-6-methyl-pyrimidin-4-yl)-4-methyl-thiazol-2-yl]-urea Sodium methoxide (2M in MeOH, 0.115 ml, 0.23 mmol) is added to a stirred solution of 1-[2-(5-ethyl-oxazol-2-yl)-ethyl]-3-[5-(2-methanesulfinyl-6-methyl-pyrimidin-4-yl)-4- methyl-thiazol-2-yl]-urea (Example 40) (0.050 g, 0.115 mmol) in methanol (3 ml) at room temperature. After 18 hours, the solvent is removed and the residue is dissolved in DCM and washed with water. The product is extracted into 1M HCl and the aqueous extract is washed with DCM. The aqueous phase is then basified with aq. NaOH and the product is extracted into DCM. After drying MgSO$_4$) the solvent is removed to give the titled compound.

Example 57

1-[2-(5-Ethyl-oxazol-2-yl)-ethyl]-3-{4-methyl-5-[6-methyl-2-(2-morpholin-4-yl-ethoxy)-pyrimidin-4-yl]-thiazol-2-yl}-urea Sodium hydride (0.020 mg, 0.50 mmol) is added to a stirred solution of 2-morpholin-4-yl-ethanol (0.084 ml, 0.69 mmol) and 1-[2-(5-ethyl-oxazol-2-yl)-ethyl]-3-[5-(2-methanesulfinyl-6-methyl-pyrimidin-4-yl)-4-methyl-thiazol-2-yl]-urea (Example 40) (0.10 g, 0.23 mmol). The reaction is heated at 70° C. for 8 hours then allowed to cool and filtered. The filtrate is evaporated and the residue is dissolved in DCM (50 ml) and washed with water (3×50 ml). The product is extracted into 1M HCl and the aqueous phase is washed with DCM. The aqueous phase is then basified with aq. NaOH and the product is re-extracted into DCM. After drying (MgSO$_4$) the solvent is removed to give the titled compound.

Example 58

1-[2-(1-Ethyl-1H-imidazol-4-yl)-ethyl]-3-[5-(2-methanesulfinyl-6-methyl-pyrimidin-4-yl)-4-methyl-thiazol-2-yl]-urea This compound is prepared from imidazole-1-carboxylic acid [5-(2-methanesulfinyl-6-methyl-pyrimidin-4-yl)-4-methyl-thiazol-2-yl]-amide (imidazole-urea intermediate BD) and 2-(1-ethyl-1H-imidazol-4-yl)-ethylamine (thiourea intermediate CC1) using general procedure A.

Example 59

1-(5-{2-[(2-Dimethylamino-ethyl)-methyl-amino]-6-methyl-pyrimidin-4-yl}-4-methyl-thiazol-2-yl)-3-[2-(1-ethyl-1H-imidazol-4-yl)-ethyl]-urea This material is prepared from 1-[2-(1-ethyl-1H-imidazol-4-yl)-ethyl]-3-[5-(2-methanesulfinyl-6-methyl-pyrimidin-4-yl)-4-methyl-thiazol-2-yl]-urea and N,N,N'-trimethyl-ethane-1,2-diamine using the protocol described for Example 42 but replacing DMF by dioxane.

Examples 60 & 61

These compounds, namely 1-(5-{2-[(2-dimethylamino-ethyl)-methyl-amino]-6-methyl-pyrimidin-4-yl}-4-methyl-thiazol-2-yl)-3-[2-(1-propyl-1H-imidazol-4-yl)-ethyl]-urea and 1-(5-{2-[(2-dimethylamino-ethyl)-methyl-amino]-6-methyl-pyrimidin-4-yl}-4-methyl-thiazol-2-yl)-3-[2-(1-iso-propyl-1H-imidazol-4-yl)-ethyl]-urea are prepared by analogous procedures to 1-(5-{2-[(2-dimethylamino-ethyl)-methyl-amino]-6-methyl-pyrimidin-4-yl}-4-methyl-thiazol-2-yl)-3-[2-(1-ethyl-1H-imidazol-4-yl)-ethyl]-urea (Example 59) using the appropriate starting materials.

Example 62

1-[5-(2-Cyano-6-methyl-pyrimidin-4-yl)-4-methyl-thiazol-2-yl]-3-[2-(1-isopropyl-1H-imidazol-4-yl)-ethyl]-urea Step 1) 1-[2-(1-Isopropyl-1H-imidazol-4-yl)-ethyl]-3-[4-methyl-5-(6-methyl-2-methylsulfanyl-pyrimidin-4-yl)-thiazol-2-yl]-urea This material is prepared from imidazole-1-carboxylic acid [4-methyl-5-(6-methyl-2-methyl-sulfanyl-pyrimidin-4-yl)-thiazol-2-yl]-amide (imidazole-urea intermediate BC) and 2-(1-iso-propyl-1H-imidazol-4-yl)-ethylamine (thiourea intermediate CC3) using general procedure A.

Step 2) 1-[2-(1-Isopropyl-1H-imidazol-4-yl)-ethyl]-3-[5-(2-methanesulfonyl-6-methyl-pyrimidin-4-yl)-4-methyl-thiazol-2-yl]-urea This material is prepared from 1-[2-(1-isopropyl-1H-imidazol-4-yl)-ethyl]-3[4-methyl-5-(6-methyl-2-methylsulfanyl-pyrimidin-4-yl)-thiazol-2-yl]-urea by the same protocol described for 1-[2-(5-ethyl-oxazol-2-yl)-ethyl]-3-[5-(2-methanesulfonyl-6-methyl-pyrimidin-4-yl)-4-methyl-thiazol-2-yl]-urea (Example 41).

Step 3) 1-[5-(2-Cyano-6-methyl-pyrimidin-4-yl)-4-methyl-thiazol-2-yl]-3-[2-(1-isopropyl-1H-imidazol-4-yl)-ethyl]-urea Sodium cyanide (0.069 g, 1.4 mmol) is added to a stirred solution of 1-[2-(1-isopropyl-1H-imidazol-4-yl)-ethyl]-3-[5-(2-methanesulfonyl-6-methyl-pyrimidin-4-yl)-4-methyl-thiazol-2-yl]-urea (0.21 g, 0.47 mmol) in dry DMSO (10 ml). The reaction is stirred at 50° C. under argon for 3 hours then the solvent is removed. The residue is dissolved in DCM and washed with water. The organic extract is dried (MgSO$_4$) and the solvent removed to give the titled compound.

Examples 63-72

These compounds, namely 1-[2-(2-ethyl-2H-tetrazol-5-yl)-ethyl]-3-[5-(2-methanesulfinyl-6-methyl-pyrimidin-4-yl)-4-methyl-thiazol-2-yl]-urea, 1-[5-(2-dimethylamino-6-methyl-pyrimidin-4-yl)-4-methyl-thiazol-2-yl]-3-[2-(2-ethyl-2H-tetrazol-5-yl)-ethyl]-urea, 1-(5-{2-[(2-dimethylamino-ethyl)-methyl-amino]-6-methyl-pyrimidin-4-yl}-4-methyl-thiazol-2-yl)-3-[2-(2-ethyl-2H-tetrazol-5-yl)-ethyl]-urea, N,N-dimethyl-2-{3-[4-methyl-5-(6-methyl-2-methyl-sulfanyl-pyrimidin-4-yl)-thiazol-2-yl]-ureido}-acetamide, 2-{3-[5-(2-methanesulfinyl-6-methyl-pyrimidin-4-yl)-4-methyl-thiazol-2-yl]-ureido}-N,N-dimethyl-acetamide, 2-[3-(5-{2-[(2-di-methylamino-ethyl)-methyl-amino]-6-methyl-pyrimidin-4-yl}-4-methyl-thiazol-2-yl)-ureido]-N,N-dimethyl-acetamide, 1-(5-{2-[(2-dimethylamino-ethyl)-methyl-amino]-pyrimidin-4-yl}-4-methyl-thiazol-2-yl)-3-[2-(5-ethyl-oxazol-2-yl)-ethyl]-urea, 1-[2-(5-ethyl-oxazol-2-yl)-ethyl]-3-{5-[2-(3-imidazol-1-yl-propylamino)-pyrimidin-4-yl]-4-methyl-thiazol-2-yl}-urea, 1-[2-(1-ethyl-1H-imidazol-4-yl)-ethyl]-3-[5-(2-methane-sulfinyl-pyrimidin-4-yl)-4-methyl-thiazol-2-yl]-urea and 1-(5-{2-[(2-dimethylamino-ethyl)-methyl-amino]-pyrimidin-4-yl}-4-methyl-thiazol-2-yl)-3-[2-(1-ethyl-1H-imidazol-4-yl)-ethyl]-urea are prepared from the appropriate intermediates (A, B and C) using procedures described above for similar compounds.

Examples 73-81

These compounds, namely N-[5-(2-acetylamino-pyrimidin-4-yl)-4-methyl-thiazol-2-yl]-acetamide, N-[4-methyl-5-(2-methylamino-pyrimidin-4-yl)-thiazol-2-yl]-acetamide, N-[5-(2-dimethylamino-pyrimidin-4-yl)-4-methyl-thiazol-2-yl]-acetamide, N-{4-methyl-5-[2, (2-methyl-thiazol-4-yl)-pyrimidin-4-yl]-thiazol-2-yl}-acetamide, N-[4-methyl-5-(2-phenyl-pyrimidin-4-yl)-thiazol-2-yl]-acetamide, N-[5-(2-methanesulfonyl-pyrimidin-4-yl)-4-methyl-thiazol-2-yl]-acetamide, N-[5-(2-methoxy-pyrimidin-4-yl)-4-methyl-thiazol-2-yl]-acetamide, N-[4-methyl-5-(2-pyridin-4-yl-pyrimidin-4-yl)-thiazol-2-yl]-acetamide and N-[4-methyl-5-(2-pyridin-2-yl-pyrimidin-4-yl)-thiazol-2-yl]-acetamide are prepared by an analogous procedure to N-[4-methyl-5-(2-morpholin-4-yl-pyrimidin-4-yl)-thiazol-2-yl]-acetamide (Example 25) by replacing morpholinoformamidine hydrobromide (part 25c) with the appropriate amidine.

Examples 82-86

These compounds, namely 3-{3-[5-(2-cyclopropyl-pyrimidin-4-yl)-4-methyl-thiazol-2-yl]-ureido}-propionic acid tert-butyl ester, 1-[5-(2-cyclopropyl-pyrimidin-4-yl)-4-methyl-thiazol-2-yl]-3-[2-(5-ethyl-oxazol-2-yl)-ethyl]-urea, 3-{3-[5-(2-dimethylamino-pyrimidin-4-yl)-4-methyl-thiazol-2-yl]-ureido}-propionic acid tert-butyl ester, 1-[5-(2-dimethylamino-pyrimidin-4-yl)-4-methyl-thiazol-2-yl]-3-[2-(5-ethyl-oxazol-2-yl)-ethyl]-urea, 1[5-(2-dimethylamino-pyrimidin-4-yl)-4-methyl-thiazol-2-yl]-3-[2-(3-ethyl-[1,2,4]oxadiazol-5-yl)-ethyl]-urea are prepared from aminothiazoles 5-(2-cyclopropyl-pyrimidin-4-yl)-4-methyl-thiazol-2-ylamine and [4-(2-amino-4-methyl-thiazol-5-yl)-pyrimidin-2-yl]-dimethyl-amine (which is prepared by the procedure described in Example 25d, 4-methyl-5-(2-morpholin-4-yl-pyrimidin-4-yl)-thiazol-2-ylamine, by substituting morpholinoformamidine hydrobromide in this sequence by the appropriate amidine) by reacting with 1,1'-carbonyldiimidazole (methods Ba or Bb) to give the imidazole-urea intermediates followed by reaction with the appropriate amine using general procedure A.

Example 87

N-[5-(2,6-Dimethyl-pyrimidin-4-yl)-4-methyl-thiazol-2-yl]-acetamide

This is prepared by acylating 5-(2,6-dimethyl-pyrimidin-4-yl)-4-methyl-thiazol-2-ylamine (intermediate AF) using the procedure described for N-(5-{2-[(2-dimethylamino-ethyl)-methyl-amino]-6-methyl-pyrimidin-4-yl}-4-methyl-thiazol-2-yl)-acetamide (Example 39, step 2).

Examples 88-90

These compounds, namely 1-[5-(2,6-dimethyl-pyrimidin-4-yl)-4-methyl-thiazol-2-yl]-3-[2-(5-ethyl-oxazol-2-yl)-ethyl]-urea, 1-[5-(2,6-dimethyl-pyrimidin-4-yl)-4-methyl-thiazol-2-yl]-3-[2-(1-ethyl-1H-imidazol-4-yl)-ethyl]-urea and 1-[5-(2,6-dimethyl-pyrimidin-4-yl)-4-methyl-thiazol-2-yl]-3-[2-(1-propyl-1H-imidazol-4-yl)-ethyl]-urea are prepared from imidazole-1-carboxylic acid [5-(2,6-dimethyl-pyrimidin-4-yl)-4-methyl-thiazol-2-yl]-amide (BF) using the appropriate amine (CA, CC1 & CC2).

Example 91

5-(2-tert-Butyl-pyrimidin-4-yl)-4-methyl-thiazol-2-ylamine

This compound is prepared as described previously (Intermediate AG).

Example 92

N-[5-(2-tert-Butyl-pyrimidin-4-yl)-4-methyl-thiazol-2-yl]-acetamide

This material is prepared by acylating 5-(2-tert-Butyl-pyrimidin-4-yl)-4-methyl-thiazol-2-ylamine (Intermediate AG) with acetic anhydride as described for N-(5-{2-[(2-dimethylamino-ethyl)-methyl-amino]-6-methyl-pyrimidin-4-yl}-4-methyl-thiazol-2-yl)-acetamide (Example 39, step 2).

Examples 93-96

These compounds, namely 4-[5-(2-tert-butyl-pyrimidin-4-yl)-4-methyl-thiazol-2-ylcarbamoyl]-butyric acid ethyl ester, [5-(2-tert-butyl-pyrimidin-4-yl)-4-methyl-thiazol-2-yl]-methyl-amine, 4-oxo-pentanoic acid [5-(2-tert-butyl-pyrimidin-4-yl)-4-methyl-thiazol-2-yl]-amide and 5-oxo-hexanoic acid [5-(2-tert-butyl-pyrimidin-4-yl)-4-methyl-thiazol-2-yl]-amide are prepared as follows: A mixture of 5-(2-tert-butyl-pyrimidin-4-yl)-4-methyl-thiazol-2-ylamine (aminothiazole intermediate AG, 0.297 g, 0.12 mmol) and triethylamine (0.25 ml, 1.8 mmol) in DCM (1 ml) is added to a stirred solution of the appropriate carboxylic acid (0.12 mmol), HOBT (0.0162 g, 0.12 mmol), EDCI.HCl (0.0299 g, 0.156 mmol) and triethylamine (0.025 ml, 0.18 mmol) in DCM (1 ml). After 18 hours the reaction mixture is filtered under gravity through a cartridge containing polymer supported isocyanate resin (0.5 g, pre-washed with 4 ml THF). The solvents are removed to give the titled products which are purified by HPLC if required.

Examples 97-143

These compounds, namely 1-[2-(5-tert-butyl-oxazol-2-yl)-ethyl]-3-[5-(2,6-dimethyl-pyridin-4-yl)-4-methyl-thiazol-2-yl]-urea, 4-{3-[5-(2-tert-butyl-pyrimidin-4-yl)-4-methyl-thiazol-2-yl]-ureido}-butyric acid ethyl ester, 1-[5-(2-tert-butyl-pyrimidin-4-yl)-4-methyl-thiazol-2-yl]-3-(2-propoxy-ethyl)-urea, 2-{3-[5-(2-tert-butyl-pyrimidin-4-yl)-4-methyl-thiazol-2-yl]-ureido}-N,N-dimethyl-acetamide, 3-{3-[5-(2-tert-butyl-pyrimidin-4-yl)-4-methyl-thiazol-2-yl]-ureido}-N-(2-hydroxy-1,1-dimethyl-ethyl)-propionamide, 1-[5-(2-tert-butyl-pyrimidin-4-yl)-4-methyl-thiazol-2-yl]-3-(3,3-diethoxy-propyl)-urea, N-[5-(2-tert-butyl-pyrimidin-4-yl)-4-methyl-thiazol-2-yl]-succinamic acid ethyl ester, 1-[5-(2-tert-butyl-pyrimidin-4-yl)-4-methyl-thiazol-2-yl]-3-(3-hydroxy-propyl)-urea, 1-[5-(2-tert-butyl-pyrimidin-4-yl)-4-methyl-thiazol-2-yl]-3-pyridin-2-ylmethyl-urea, 1-[5-(2-tert-butyl-pyrimidin-4-yl)-4-methyl-thiazol-2-yl]-3-pyridin-3-ylmethyl-urea, 1-[5-(2-tert-butyl-pyrimidin-4-yl)-4-methyl-thiazol-2-yl]-3-pyridin-4-ylmethyl-urea, 1-[5-(2-tert-butyl-pyrimidin-4-yl)-4-methyl-thiazol-2-yl]-3-(2-methoxy-ethyl)-urea, 1-[5-(2-tert-butyl-pyrimidin-4-yl)-4-methyl-thiazol-2-yl]-3-(2-hydroxy-ethyl)-urea, 1-[5-(2-tert-butyl-pyrimidin-4-yl)-4-methyl-thiazol-2-yl]-3-(4- hydroxy-butyl)-urea, 1-[5-(2-tert-butyl-pyrimidin-4-yl)-4-methyl-thiazol-2-yl]-3-(2-dimethylamino-ethyl)-urea, 1-[5-(2-tert-butyl-pyrimidin-4-yl)-4-methyl-thiazol-2-yl]-3-(2-pyrrolidin-1-yl-ethyl)-urea, 1-[5-(2-tert-butyl-pyrimidin-4-yl)-4-methyl-thiazol-2-yl]-3-(2-piperidin-1-yl-ethyl)-urea, 1-[5-(2-tert-butyl-pyrimidin-4-yl)-4-methyl-thiazol-2-yl]-3-(3-morpholin-4-yl-propyl)-urea, 1-[5-(2-tert-butyl-pyrimidin-4-yl)-4-methyl-thiazol-2-yl]-3-(2-diethylamino-ethyl)-urea, 1-[5-(2-tert-butyl-pyrimidin-4-yl)-4-methyl-thiazol-2-yl]-3-(2-oxo-tetrahydro-furan-3-yl)-urea, 1-[5-(2-tert-butyl-pyrimidin-4-yl)-4-methyl-thiazol-2-yl]-3-[2-(1-methyl-pyrrolidin-2-yl)-ethyl]-urea, 1-[5-(2-tert-butyl-pyrimidin-4-yl)-4-methyl-thiazol-2-yl]-3-[2-(2-hydroxy-ethoxy)-ethyl]-urea, 1-[5-(2-tert-butyl-pyrimidin-4-yl)-4-methyl-thiazol-2-yl]-3-(1-methyl-1H-pyrrol-2-ylmethyl)-urea, 1-[5-(2-tert-butyl-pyrimidin-4-yl)-4-methyl-thiazol-2-yl]-3-(2-ethoxy-ethyl)-urea, 1[5-(2-tert-butyl-pyrimidin-4-yl)-4-methyl-thiazol-2-yl]-3-(2-hydroxy-1-methyl-ethyl)-urea, 1-[5-(2-tert-butyl-pyrimidin-4-yl)-4-methyl-thiazol-2-yl]-3-(2-methoxy-1-methyl-ethyl)-urea, 2-{3-[5-(2-tert-butyl-pyrimidin-4-yl)-4-methyl-thiazol-2-yl]-ureido}-propionic acid ethyl ester, 1-[5-(2-tert-butyl-pyrimidin-4-yl)-4-methyl-thiazol-2-yl]-3-(2,2-diethoxy-ethyl)-urea, 1-[5-(2-tert-butyl-pyrimidin-4-yl)-4-methyl-thiazol-2-yl]-3-(3-isopropoxy-propyl)-urea, 1-[5-(2-tert-butyl-pyrimidin-4-yl)-4-methyl-thiazol-2-yl]-3-(3-ethoxy-propyl)-urea, 1-[5-(2-tert-butyl-pyrimidin-4-yl)-4-methyl-thiazol-2-yl]-3-(2,3-di-hydroxy-propyl)-urea, 2-{3-[5-(2-tert-butyl-pyrimidin-4-yl)-4-methyl-thiazol-2-yl]-ureido}-2-methyl-propionic acid tert-butyl ester, 3-methanesulfonyl-pyrrolidine-1-carboxylic acid [5-(2-tert-butyl-pyrimidin-4-yl)-4-methyl-thiazol-2-yl]-amide, 1-[5-(2-tert-butyl-pyrimidin-4-yl)-4-methyl-thiazol-2-yl]-3-(2-pyridin-2-yl-ethyl)-urea, 1-[5-(2-tert-butyl-pyrimidin-4-yl)-4-methyl-thiazol-2-yl]-3-(2-hydroxy-1,1-dimethyl-ethyl)-urea, 3-{3-[5-(2-tert-butyl-pyrimidin-4-yl)-4-methyl-thiazol-2-yl]-ureido}-N-(2-oxo-tetrahydro-furan-3-yl)-propionamide, pyrrolidine-1,2-dicarboxylic acid 2-amide 1-{[5-(2-tert-butyl-pyrimidin-4-yl)-4-methyl-thiazol-2-yl]-amide}, 1,4,6,7-tetrahydro-imidazo[4,5-c]pyridine-5-carboxylic acid [5-(2-tert-butyl-pyrimidin-4-yl)-4-methyl-thiazol-2-yl]-amide, 3-hydroxy-pyrrolidine-1-carboxylic acid [5-(2-tert-butyl-pyrimidin-4-yl)-4-methyl-thiazol-2-yl]-amide, 3-hydroxy-pyrrolidine-1-carboxylic acid [5-(2-tert-butyl-pyrimidin-4-yl)-4-methyl-thiazol-2-yl]-amide, 1-[5-(2-tert-butyl-pyrimidin-4-yl)-4-methyl-thiazol-2-yl]-3-(1H-pyrazol-3-yl)-urea, 1-[5-(2-tert-butyl-pyrimidin-4-yl)-4-methyl-thiazol-2-yl]-3-(2-imidazol-1-yl-ethyl)-urea, 1-[5-(2-tert-butyl-pyrimidin-4-yl)-4-methyl-thiazol-2-yl]-3-[2-(1-isopropyl-1H-imidazol-4-yl)-ethyl]-urea, 3-{3-[5-(2-tert-butyl-pyrimidin-4-yl)-4-methyl-thiazol-2-yl]-ureido}-N-(3-hydroxy-2,2-dimethyl-propyl)-propionamide, 1-[5-(2-tert-butyl-pyrimidin-4-yl)-4-methyl-thiazol-2-yl]-3-(2,3-dihydroxy-propyl)-urea, 1-[5-(2-tert-butyl-pyrimidin-4-yl)-4-methyl-thiazol-2-yl]-3-(2,3-dihydroxy-propyl)-urea, and 1-[5-(2-tert-butyl-pyrimidin-4-yl)-4-methyl-thiazol-2-yl]-3-(5-isopropyl-[1,3,4]oxadiazol-2-ylmethyl)-urea are prepared from imidazole-1-carboxylic acid [5-(2-tert-butyl-pyrimidin-4-yl)-4-methyl-thiazol-2-yl]-amide (imidazole-urea intermediate BG) and the appropriate amine (amine intermediate C) using general procedure A.

Examples 144-146

These compounds, namely [5-(2-tert-butyl-pyrimidin-4-yl)-4-methyl-thiazol-2-yl]-pyrazin-2-yl-amine, (5-bromo-[1,3,4]thiadiazol-2-yl)-[5-(2-tert-butyl-pyrimidin-4-yl)-4-methyl-thiazol-2-yl]-amine and [5-(2-tert-butyl-pyrimidin-4-yl)-4-methyl-thiazol-2-yl]-(6-methyl-pyridin-2-yl)-amine are prepared by reaction of the appropriate thiourea intermediate (DA, DB, DC) with 1-bromo-1-(2-tert-butyl-pyrimidin-4-yl)-propan-2-one (aminothiazole intermediate AG3) following the procedure described for the preparation of 5-(2-tert-butyl-pyrimidin-4-yl)-4-methyl-thiazol-2-ylamine (AG4) in Example 91.

The invention claimed is:
1. A compound of formula I

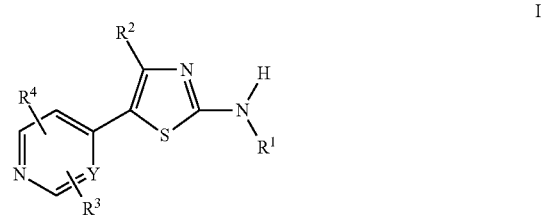

in free or salt form, wherein
$R^1$ is —CO—$NR^xR^y$, where $R^x$ and $R^y$ together with the nitrogen to which they are attached form a substituted or unsubstituted 5- to 12-membered N-heterocyclic ring optionally including one or more ring hetero atoms selected from the group consisting of oxygen, nitrogen and sulphur; wherein the optional substituent is selected from hydroxy, —$SO_2$—$CH_3$ or aminocarbonyl;
$R^2$ is $C_1$-$C_3$-alkyl;
Y is nitrogen; and
$R^3$ and $R^4$ are each independently hydrogen, halo, hydroxy, cyano, amino, carboxy, $C_1$-$C_8$-alkylsulfanyl, $C_1$-$C_8$-alkylsulfinyl, $C_1$-$C_8$-alkylsulfonyl, —$SO_2NH_2$, $C_1$-$C_8$-alkyl, $C_1$-$C_8$-haloalkyl, amino-$C_1$-$C_8$-alkyl, amino-$C_1$-$C_8$-alkoxy, $C_1$-$C_8$-alkylaminocarbonyl, di($C_1$-$C_8$-alkyl)aminocarbonyl, di($C_1$-$C_8$-alkyl)amino-$C_1$-$C_8$-alkyl, di($C_1$-$C_8$-alkyl)amino-$C_1$-$C_8$-alkoxy, $C_1$-$C_8$-acylamino, aminocarbonyl, $C_1$-$C_8$-alkoxycarbonyl, carboxy-$C_1$-$C_8$-alkyl, carboxy-$C_1$-$C_8$-alkoxy, a $C_3$-$C_{15}$-carbocycle, a 5- or 6-membered heterocyclic ring having one or more ring hetero atoms selected from the group consisting of oxygen, nitrogen and sulphur, $C_1$-$C_8$-alkylamino or di($C_1$-$C_8$-alkyl)amino each being optionally substituted by amino, hydroxy, di($C_1$-$C_8$-alkyl)amino or a 5- or 6-membered heterocyclic ring having one or more ring hetero atoms selected from the group consisting of oxygen, nitrogen and sulphur, or $C_1$-$C_8$-alkoxy optionally substituted by a 5- or 6-membered heterocyclic ring having one or more ring hetero atoms selected from the group consisting of oxygen, nitrogen and sulphur.

2. A compound according claim 1 wherein
$R^1$ is —CO—$NR^xR^y$, where $R^x$ and $R^y$ together with the nitrogen to which they are attached form a substituted or unsubstituted 5- to 12-membered N-heterocyclic ring optionally including one or more ring hetero atoms selected from the group consisting of oxygen, nitrogen and sulphur, wherein the optional substituent is selected from hydroxy, —$SO_2$—$CH_3$ or aminocarbonyl.

3. A compound according to claim 2 wherein the 5- to 12-membered N-heterocyclic ring is substituted by hydroxy, —$SO_2$—$CH_3$ or aminocarbonyl.

4. A compound according claim 1 wherein
$R^1$ is —CO—$NR^xR^y$, where $R^x$ and $R^y$ together with the nitrogen to which they are attached form a substituted or unsubstituted 5- to 12-membered N-heterocyclic ring selected from pyrrolidine, morpholino and tetrahydro-imidazo-pyridine; wherein the optional substituent is selected from hydroxy, —SO$_2$—CH$_3$ or aminocarbonyl.

5. A compound according to claim 4 wherein
R$^1$ is —CO—NR$^x$R$^y$, where R$^x$ and R$^y$ together with the nitrogen to which they are attached form a substituted or unsubstituted 5- to 9-membered N-heterocyclic ring optionally including one or more ring hetero atoms selected from the group consisting of oxygen, nitrogen and sulphur; wherein the optional substituent is selected from hydroxy, —SO$_2$—CH$_3$ or aminocarbonyl.

6. A compound of formula XXI

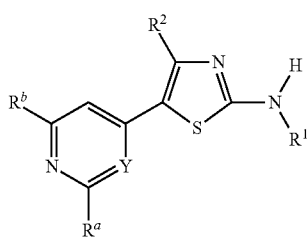

XXI where R$^1$, Y, R$^a$ and R$^b$ are as shown in the following table:

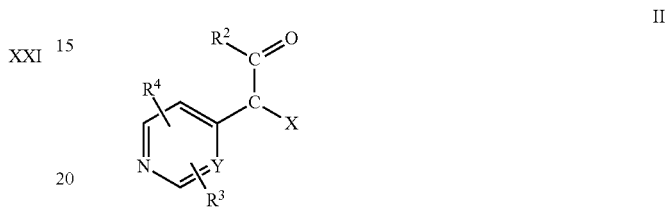

7. A compound according to claim 1 in combination with another drug substance which is an anti-inflammatory, a bronchodilator, an antihistamine, a decongestant or an anti-tussive drug substance.

8. A pharmaceutical composition comprising as active ingredient a compound according to claim 1.

9. A method for the treatment of asthma in a subject in need of such treatment, which comprises administering to said subject an effective amount of a compound of formula I as defined in claim 1 in free form or in the form of a pharmaceutically acceptable salt.

10. A process for the preparation of a compound of formula I as defined in claim 1, in free or salt form which comprises the steps of:
(i) (A) reacting a compound of formula II

II wherein R$^2$, R$^3$, R$^4$ and Y are as hereinbefore defined and X is halogen, with a compound of formula III

III wherein R$^1$ is as hereinbefore defined;
(B) for the preparation of compounds of formula I where R$^3$ is a 5- or 6-membered N-heterocyclic ring having one or more ring hetero atoms selected from the group consisting of oxygen, nitrogen and sulphur, reacting a compound of formula I wherein R$^1$, R$^2$, R$^4$ and Y are as hereinbefore defined and R$^3$ is chloro or bromo, with a compound of formula IV

IV

R$^5$
   \
    N—H
   /
R$^6$ wherein R$^5$ and R$^6$ together form a 5- or 6-membered N-heterocyclic ring having one or more ring hetero atoms selected from the group consisting of oxygen, nitrogen and sulphur;
(C) for the preparation of compounds of formula I where R$^3$ is C$_1$-C$_8$-alkylamino optionally substituted by hydroxy or di(C$_1$-C$_8$-alkyl)amino, reacting a compound of formula I wherein R$^1$, R$^2$, R$^4$ and Y are as hereinbefore defined and R$^3$ is chloro or bromo, with a compound of formula V

R$^7$—NH$_2$     V wherein R$^7$ is C$_1$-C$_8$-alkyl optionally substituted by hydroxy or di(C$_1$-C$_8$-alkyl)amino;
(D) for the preparation of compounds of formula I where R$^3$ is C$_1$-C$_8$-alkylsulfinyl or C$_1$-C$_8$-alkylsulfonyl, oxidising the corresponding C$_1$-C$_8$-alkylsulfanyl or C$_1$-C$_8$-alkylsulfinyl respectively;

(E) for the preparation of compounds of formula I where $R^3$ is di($C_1$-$C_8$-alkyl)amino optionally substituted by amino, hydroxy, di($C_1$-$C_8$-alkyl)amino or a 5- or 6-membered heterocyclic ring having one or more ring hetero atoms selected from the group consisting of oxygen, nitrogen and sulphur, reacting the corresponding compound where $R^3$ is $C_1$-$C_8$-alkylsulfinyl or $C_1$-$C_8$-alkylsulfonyl with a compound of formula Xa

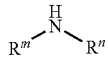 Xa or a protected form thereof where $R^m$ and $R^n$ are independently $C_1$-$C_8$-alkyl optionally substituted by amino, hydroxy, di($C_1$-$C_8$-alkyl)amino or a 5- or 6-membered heterocyclic ring having one or more ring hetero atoms selected from the group consisting of oxygen, nitrogen and sulphur;

(F) for the preparation of compounds of formula I where $R^3$ is $C_1$-$C_8$-alkoxy, reacting the corresponding compound where $R^3$ is $C_1$-$C_8$-alkylsulfinyl with an alkali metal $C_1$-$C_8$-alkoxide;

(G) for the preparation of compounds of formula I where $R^3$ is $C_1$-$C_8$-alkoxy substituted by a 5- or 6-membered heterocyclic ring having one or more ring hetero atoms selected from the group consisting of oxygen, nitrogen and sulphur, reacting the corresponding compound where $R^3$ is $C_1$-$C_8$-alkylsulfinyl with a compound of formula Xb

 Xb where V is $C_1$-$C_8$-alkyl and $T^2$ is a 5- or 6-membered heterocyclic ring having one or more ring hetero atoms selected from the group consisting of oxygen, nitrogen and sulphur in the presence of a base; or (H) for the preparation of compounds of formula I where $R^3$ is cyano, reducing the corresponding compound where $R^3$ is $C_1$-$C_8$-alkylsulfonyl with an alkali metal cyanide; and (ii) removing any protecting groups and recovering the resultant compound of formula I in free or salt form.

\* \* \* \* \*